(12) United States Patent
Ko

(10) Patent No.: US 8,334,253 B2
(45) Date of Patent: Dec. 18, 2012

(54) COSMETIC AND DERMATOLOGICAL FORMULATIONS OF MNTF PEPTIDES

(75) Inventor: Pui-Yuk Dorothy Ko, Monterey Park, CA (US)

(73) Assignee: Dermacare Neuroscience Institute, Beverly Hills, CA (US)

( * ) Notice: Subject to any disclaimer, the term of this patent is extended or adjusted under 35 U.S.C. 154(b) by 743 days.

(21) Appl. No.: 12/391,243

(22) Filed: Feb. 23, 2009

(65) Prior Publication Data

US 2009/0274752 A1     Nov. 5, 2009

Related U.S. Application Data

(60) Provisional application No. 61/066,670, filed on Feb. 21, 2008.

(51) Int. Cl.
| | |
|---|---|
| *A61K 38/00* | (2006.01) |
| *A61K 51/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |

(52) U.S. Cl. ......... 514/1.1; 530/300; 530/333; 424/1.69
(58) Field of Classification Search .................. None
See application file for complete search history.

(56) References Cited

FOREIGN PATENT DOCUMENTS

WO    WO2004065410    *   8/2004

* cited by examiner

*Primary Examiner* — Maury Audet
(74) *Attorney, Agent, or Firm* — James W. Collett

(57) ABSTRACT

The disclosure is directed to methods and compositions that include MNTF peptides and their analogs for cosmetic and dermatological purposes.

14 Claims, 9 Drawing Sheets

SEQUENCE LISTING

```
<160> NUMBER OF SEQ ID NOS: 27

<210> SEQ ID NO 1
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                            Synthetic peptide"

<400> SEQUENCE: 1

Leu Gly Thr Phe Trp Gly Asp Thr Leu Asn Cys Trp Met Leu Ser Ala
1               5                   10                  15

Phe Ser Arg Tyr Ala Arg Cys Leu Ala Glu Gly His Asp Gly Pro Thr
            20                  25                  30

Gln

<210> SEQ ID NO 2
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Phe Ser Arg Tyr Ala Arg
1               5

<210> SEQ ID NO 3
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Trp Met Leu Ser Ala Phe Ser
1               5

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Met Leu Ser Ala Phe Ser Arg Tyr Ala Arg
1               5                   10

<210> SEQ ID NO 5
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Phe Ser Arg Tyr Ala Arg Cys Leu Ala Glu Gly
1               5                   10

<210> SEQ ID NO 6
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 6

Cys Trp Met Leu Ser Ala Phe Ser Arg Tyr Ala Arg Cys
1               5                   10

<210> SEQ ID NO 7
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Met Leu Ser Ala Phe Ser Arg Tyr Ala Arg Cys Leu Ala Glu Gly His
1               5                   10                  15

Asp Gly Pro Thr Gln
            20

<210> SEQ ID NO 8
<211> LENGTH: 2
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Phe Ser
1

<210> SEQ ID NO 9
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Phe Ser Arg
1

<210> SEQ ID NO 10
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ala Phe Ser
1

<210> SEQ ID NO 11
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 11

Phe Ser Arg Tyr
1

<210> SEQ ID NO 12
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ser Ala Phe Ser
1

<210> SEQ ID NO 13
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ala Phe Ser Arg
1

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Leu Ser Ala Phe Ser
1               5

<210> SEQ ID NO 15
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Ala Phe Ser Arg
1               5

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ala Phe Ser Arg Tyr
1               5
```

```
<210> SEQ ID NO 17
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Phe Ser Arg Tyr Ala
1               5

<210> SEQ ID NO 18
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Met Leu Ser Ala Phe Ser
1               5

<210> SEQ ID NO 19
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Leu Ser Ala Phe Ser Arg
1               5

<210> SEQ ID NO 20
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Ala Phe Ser Arg Tyr
1               5

<210> SEQ ID NO 21
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ala Phe Ser Arg Tyr Ala
1               5

<210> SEQ ID NO 22
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 22

Ser Arg Tyr Ala Arg
1               5

<210> SEQ ID NO 23
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Arg Tyr Ala Arg
1

<210> SEQ ID NO 24
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Tyr Ala Arg
1

<210> SEQ ID NO 25
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ser Arg Tyr Ala
1

<210> SEQ ID NO 26
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Arg Tyr Ala
1

<210> SEQ ID NO 27
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 27

Ser Arg Tyr
1
```

COSMETIC AND DERMATOLOGICAL FORMULATIONS OF MNTF PEPTIDES

CROSS REFERENCE TO RELATED APPLICATIONS

This application claims priority from U.S. Provisional Application No. 61/066,670, filed Feb. 21, 2008 and entitled "Cosmetic and Dermatological Formulations of Motoneurotrophic Factor Peptides", the contents of which is hereby incorporated by reference in its entirety.

BACKGROUND OF THE DISCLOSURE

The present disclosure relates generally to cosmetic and dermatological formulations containing peptides that improve the appearance of skin, reduce or inhibit environmental damage to skin, or some combination of these.

Ultraviolet radiation (UV) is a major causal factor for skin (cutaneous) aging. It's been reported that repeated exposure to ultraviolet radiation (e.g. sunlight) can cause the skin to age prematurely, a condition which has been termed "photo-aging" (John J. Voorhees, New England J. Med, Nov. 13, 1997). Photo-aged skin can be characterized by wrinkles, presence of brown spots, changes in pigmentation and/or surface roughness. These changes are not part of the natural, normal aging process of the dermal tissue. In addition, exposure to environmental factors such as smog, consumption of alcohol, tobacco, and stress can also lead to pre-mature aging of the skin. Furthermore, inflammatory response associated with various skin injuries (e.g. cuts, burns) and dermatological conditions (e.g. skin infections, acne) can also contribute to pre-mature skin aging.

The cosmetic industry is continuously searching for novel ingredients to counter the adverse effects of premature skin aging as well as ways to reduce undesirable effects associated with skin inflammation where possible. Thus, it is desirable to have novel cosmetic and/or dermatological compositions to counter conditions associated with pre-mature skin aging.

General Aspects of UV And Free Radical Induced Skin Aging

There are a variety of causal factors for accumulated cellular damage in the skin that lead to premature skin aging. Among these are the oxidative processes and related free radical damage that result from UV lights (e.g. sunlight), smog, toxins, cigarette smoke, X-rays, drugs, and other environmental stressors. Although sunscreens can be used to reduce skin cancer and sunburn, they may not fully protect against skin photo-aging, since sunburn and photo-aging can be caused by different types of ultraviolet (e.g. UVA, UVB, UVC) light as well as damages arising from certain UV induced reactive oxygen species Typically, when skin is exposed to these potentially damaging changes, there is sufficient cellular energy adenosine triphosphate (ATP) for cellular repair and/or renewal. However, as an individual ages, enzymes that provide antioxidant activity such as superoxide dismutase (SOD) and catalase become less available, leading to decrease in antioxidant enzymes to combat free radicals, reactive oxygen species, and/or peroxides. Organs such as the hands, face, neck, and arms are areas usually chronically exposed to light and this continuous exposure to sunlight can lead to generation of free radicals in the dermal layer.

Certain dermal components are especially susceptible to free radical induced oxidative stress or the concomitant and/or subsequent inflammatory alterations in the dermis. The skin protein collagen is particularly susceptible to free radical damage and the resultant cross-collagen linking. Collagen cross-linking can be characterized by the transition of normally elastic/mobile collagen to become stiff and less elastic/mobile. The result is an aging appearance (e.g. wrinkles) and reduced tonicity in the skin. In addition, presence of acne has also been linked to free radical/peroxide production.

It is well recognized in the art that antioxidants are able to donate an electron to a free radical, stabilizing the free radical and stopping the chain of chemical reactions and potential damage. In a similar manner, antioxidants can prevent free radical damage which can slow the aging process.

The survival of embryonic motoneurons has been found to be dependent upon specific trophic substances derived from the associated developing skeletal muscles. Certain skeletal muscles have been reported to produce substances that are capable of enhancing the survival and development of motoneurons by preventing the embryonic motoneurons from degeneration and subsequent, natural cellular death. These substances have been broadly described as neuronotrophic factors (NTFs), which are a specialized group of proteins which function to promote the survival, growth, maintenance, and functional capabilities of selected populations of neurons (e.g., Chau et al., 1990, Chin. J. Neuroanat. 6:129).

U.S. Pat. No. 6,309,877, U.S. Pat. No. 7,183,373, U.S. Pat. No. 6,841,531, U.S. Pat. No. 6,759,389 and US20060052299 disclose motoneuronotrophic factors (MNTFs), which are peptides that exhibit trophic effects on motoneurons.

BRIEF SUMMARY

The invention stems from the unexpected discovery that MNTF peptides and MNTF peptide analogs, when administered to skin, inhibit and reduce photodamage, oxidative damage, wrinkling and other symptoms of skin aging and related conditions. The peptides can be used to enhance the appearance of skin, such as by improving skin tone, reducing scarring, reducing or inhibiting keloid formation, and promoting skin regeneration.

This invention describes novel MNTF peptides, in derivatized and non-derivatized forms, which exhibit such properties. The disclosure also describes use of MNTF peptides described elsewhere, which also exhibit such properties. In one embodiment, the invention is directed to a topical composition comprising an MNTF peptide having an amino acid sequence comprising at least residues 17 and 18 of SEQ ID NO: 1, and a cosmetically, dermatologically or pharmaceutically acceptable carrier. In certain embodiments of the topical composition, the MNTF peptide or analog thereof is selected from the group consisting of SEQ ID NO:1-SEQ ID NO:27, or a functional derivative thereof. In certain embodiments of the topical composition, the MNTF peptide or analog thereof is selected from the group consisting of any one of SEQ ID NOS. 2 and 8-21, or a functional derivative thereof.

In one embodiment, a MNTF peptide or analog thereof is N-terminally modified by covalent linkage with a penetration enhancer whereby the ability of the composition to penetrate into the skin is improved. Penetration enhancers may comprise lipophylic moieties. One suitable penetration enhancer is a fatty acid chain of 2 to 22 carbons, where the fatty acid chain is hydroxylated or non-hydroxylated, saturated or unsaturated, linear or branched, sulfurated or non-sulfurated, cyclic or non-cyclic; or a biotin group; or a protective group selected from the group consisting of benzyloxycarbonyl (Z), terbutyloxycarbonyl (tBoc), fluorenylmethyloxycarbonyl (Fmoc), and allyloxy-carbonyl (Alloc) groups. Preferred fatty acids and salts thereof useful as penetration enhancers include, but are not limited to cabrylic acid, oleic acid, lauric acid, capric acid, caprylic acid, hexanoic acid, myristic acid, palmitic acid, valeric acid, stearic acid, linoleic acid, linolenic acid, arachidonic acid, oleic acid, elaidic acid, erucic acid, nervonic acid. Alkyl chains of from about 2 to 22 carbons are also suitable penetration enhancers.

Also provided are compositions where a MNTF peptide is i) encapsulated in a vector selected from the group consisting of macro-capsules, micro-capsules, nano-capsules, liposomes, chylomicrons and microsponges, or ii) absorbed on a material selected from the group consisting of powdered organic polymers, talcs, bentonites, and other mineral supports, or iii) mixed with other ingredients selected from a group comprising extracted lipids, vegetable extracts, liposoluble active principles, hydrosoluble active principles, anhydrous gels, emulsifying polymers, tensioactive polymers, synthetic lipids, gelifying polymers, tissue extracts, marine extracts, Vitamin A, Vitamin C, Vitamin D, Vitamin E, solar filters, and antioxidants.

Preferably, the MNTF compositions provided herein comprise a MNTF peptide in an amount effective to promote the rejuvenation or protection of skin. The composition may be administered with a cosmetically, dermatologically or pharmaceutically acceptable carrier, preferably as a topical formulation.

The invention includes methods for administering compositions that include MNTF peptides or analogs thereof for cosmetic, anti-inflammation, anti-oxidative damage, anti-photoaging, or anti-wrinkle purposes, or for some combination of these purposes.

Another aspect of the invention is directed to methods for rejuvenating or protecting skin by administering a MNTF composition. These methods may further comprise reducing or inhibiting photodamage associated inflammation or free radical damage, reducing peroxides or free radical generation in the skin, reducing wrinkles, improving skin tone, reducing UV or photodamage, promoting skin regeneration.

Another aspect of the invention is directed to a method for improving an acne scar by topically administering a MNTF composition in an amount effective to improve or reduce the acne scarring.

Another aspect of the invention is directed to methods for reducing keloid formation in a subject by administering a MNTF composition in an amount effective to reduce the keloid formation.

The MNTF peptide and MNTF peptide analogs are based on the sequence SEQ ID NO: 1, which is a 33-mer peptide (i.e., 33 residue polypeptide) that has been previously disclosed elsewhere. As described herein, the MNTF peptide and MNTF peptide analogs useful in the compositions and methods described herein preferably include as few as two, and as many as all 33 consecutive amino acid residues of SEQ ID NO: 1. In preferred embodiments, the MNTF peptide and MNTF peptide analogs described herein include at least the FS (SEQ ID NO: 8) residues present at residues 17 and 18 of SEQ ID NO: 1.

In another embodiment, the MNTF peptide or analog thereof comprises the phenylalanine-serine dipeptide of SEQ ID NO: 1 and from 1-30 additional amino acids of SEQ ID NO: 1, said MNTF peptide or analog thereof optionally having from 1-5 conservative amino acid substitutions of the sequence depicted in SEQ ID NO: 1, or an ester, amide, prodrug and/or salt form thereof.

In other embodiments, an MNTF peptide thereof consists of i) between 2 and 6 consecutive amino acids of SEQ ID NO: 1; ii) between 2 and 5 consecutive amino acids of SEQ ID NO: 1; iii) between 3 and 5 consecutive amino acids of SEQ ID NO: 1; iv) at least 2 consecutive amino acids of SEQ ID NO: 1; v) at least 3 consecutive amino acids of SEQ ID NO: 1, or vi) an analog of any thereof, such as a functional derivative of any of i)-v). The MNTF peptide in i), iv) and v) does not have an amino acid sequence consisting of SEQ ID NO: 2. By way of example, suitable MNTF peptide and MNTF peptide analogs can have the amino acid sequence of any one of SEQ ID NOS: 1-27.

| | |
|---|---|
| LGTFWGDTLN CWMLSAFSRY ARCLAEGHDG PTQ | (SEQ ID NO: 1) |
| FSRYAR | (SEQ ID NO: 2) |
| WMLSAFS | (SEQ ID NO: 3) |
| MLSAFSRYAR | (SEQ ID NO: 4) |
| FSRYARCLAE G | (SEQ ID NO: 5) |
| CWMLSAFSRY ARC | (SEQ ID NO: 6) |
| MLSAFSRYAR CLAEGHDGPT Q | (SEQ ID NO: 7) |
| FS | (SEQ ID NO: 8) |
| FSR | (SEQ ID NO: 9) |
| AFS | (SEQ ID NO: 10) |
| FSRY | (SEQ ID NO: 11) |
| SAFS | (SEQ ID NO: 12) |
| AFSR | (SEQ ID NO: 13) |
| LSAFS | (SEQ ID NO: 14) |
| SAFSR | (SEQ ID NO: 15) |
| AFSRY | (SEQ ID NO: 16) |
| FSRYA | (SEQ ID NO: 17) |
| MLSAFS | (SEQ ID NO: 18) |
| LSAFSR | (SEQ ID NO: 19) |
| SAFSRY | (SEQ ID NO: 20) |
| AFSRYA | (SEQ ID NO: 21) |
| SRYAR | (SEQ ID NO: 22) |
| RYAR | (SEQ ID NO: 23) |
| YAR | (SEQ ID NO: 24) |
| SRYA | (SEQ ID NO: 25) |
| RYA | (SEQ ID NO: 26) |
| SRY | (SEQ ID NO: 27) |

DETAILED DESCRIPTION

Figure 1:
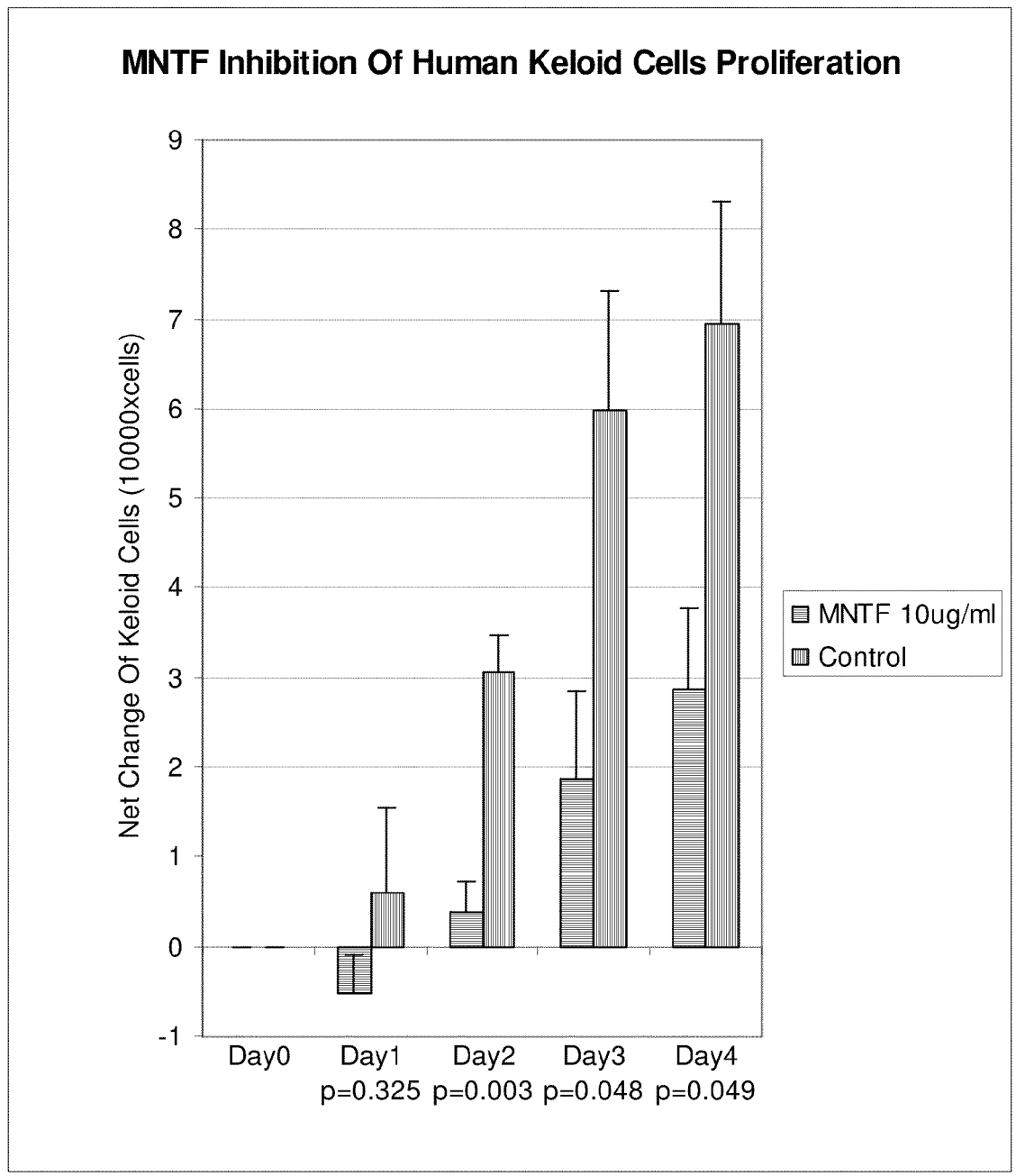
FIG. 1 is a bar graph that illustrates the dose-dependent reduction/inhibition in the proliferation of human keloid fibroblasts in response to an MNTF peptide described herein (Pal-Hexapeptide).

This disclosure relates to the unexpected discovery that compositions that include an MNTF peptide (i.e., a portion of MNTF protein, which has previously been described as exhibiting neurotrophic activities), have important dermatological and cosmetic uses. Such compositions include cosmetically- and dermatologically-applicable compositions (e.g., topically-applied formulations of the MNTF peptides described herein).

Disclosed herein are peptides derived from MNTF that exhibit cosmetically and dermatologically beneficial properties. The peptides are referred to herein alternatively and interchangeably as "MNTF peptides" and "dermal factor peptides." Methods of making and using compositions including one or more such peptides, the compositions being useful for cosmetic and dermatological purposes, are described.

The present disclosure includes cosmetic compositions that are effective for reducing the appearance of wrinkles, acne, and other dermal scars. Such compositions are also useful for stimulating collagen renewal, improving skin tonicity (i.e., they soften skin, firm skin, or both), otherwise improving the skin appearance (e.g., skin radiance), and oxidative and radiation-induced damage to skin.

The compositions described herein can be administered topically to skin to stimulate production of skin fibroblast in order to achieve a variety of cosmetic and dermatological outcomes. Such administration can rebuild dermal matrix molecules, regenerate the skin's upper layers by stimulating collagen production, thickening the epidermis, and suppress inflammation mediators (e.g., interleukins) that trigger inflammation, and to otherwise inhibit or prevent oxidative and inflammatory damage to skin.

Exposure to harmful radiation (e.g., UV light or sunlight) can cause release of inflammatory mediators (e.g., interleukins) in the dermal layer, which can lead to creation of active inflammatory products and to inflammation in skin and nearby tissues. The compositions described herein exhibit anti-inflammatory, anti-oxidative (e.g., anti-free-radical) properties when applied topically to the skin of a subject.

The disclosure includes a method of protecting skin against the symptoms of aging (e.g., aging symptoms associated with exposure to UV light). Such methods involve applying to the skin a preparation comprising an MNTF peptide or analog thereof described herein. These compositions offer protection against symptoms associated with UV-A, UV-B and UV-C types of ultraviolet light, for example.

The compositions described herein can be used to inhibit, prevent, or reduce cosmetic or dermatological changes in skin. Such use involves applying an MNTF peptide or analog thereof described herein to the skin, preferably in a cosmetic or dermatological preparation. Cosmetic and dermatological changes to skin that can be inhibited, reduced, or prevented include changes in the appearance and/or tonicity of the skin, such as development of wrinkles or brown spots.

Compositions described herein can be used to promote skin hydration and for general skin care (i.e., ordinary maintenance of skin). The compositions can inhibit, reduce or prevent sun burn, wrinkles, photo-damage, acne, other conditions associated with cutaneous aging, heliodermia, free radical damage, and inflammation in skin to which the compositions are applied.

In one embodiment, the disclosure relates to a cosmetic or dermatological wipe (e.g., a pad, towelette, swab, or other absorbent material) containing, coated with, or impregnated with a composition described herein. Such wipes are convenient devices for topically applying the compositions described herein to skin.

MNTF Peptides And Analogs Thereof

The cosmetic and dermatological compositions described herein include at least one MNTF peptide or analog thereof. The MNTF peptides and analogs thereof that are useful for the purposes described in this disclosure include at least two consecutive amino acid residues of the portion of the MNTF molecule represented by the amino acid sequence SEQ ID NO: 1. In preferred embodiments, the peptides include at least the FS (phenylalanine and serine) (SEQ ID NO: 8) residues that are present at residues 17 and 18 of SEQ ID NO: 1. The peptides and analogs thereof can include additional consecutive amino acid residues of SEQ ID NO: 1, on either the amino-terminal or carboxyl-terminal end of the FS (SEQ ID NO: 8) residues. Examples of suitable MNTF peptides include those reported in U.S. Pat. No. 6,309,877, U.S. Pat. No. 7,183,373, U.S. Pat. No. 6,841,531, U.S. Pat. No. 6,759,389, and US Patent application publication number 2006/0052299.

MNTF peptides and peptide analogs described herein include peptides derived from MNTF (i.e., peptides having two or more consecutive residues of SEQ ID NO: 1) and functional derivatives of such peptides. Suitable examples of MNTF peptides include those having the amino acid sequence of one of SEQ ID NOs: 1-27, and functional derivatives of those peptides. The MNTF peptides and analogs thereof can be used as salts, esters, and other ordinary dosage forms. Suitable analogs include, for example, peptides in which one or more of the amino acid residues has been replaced by a non-naturally-occurring (e.g., D-isomer) amino acid residue. Other analogs include peptides in which one or more amino acid residues of SEQ ID NO: 1 are replaced with a synonymous amino acid residue, such those described in Tables I, II, and III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |

TABLE I-continued

Preferred Groups of Synonymous Amino Acids

| Amino Acid | Synonymous Group |
|---|---|
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Ile, Phe, Met, Leu |
| Pro | Ala, Pro |
| Thr | Thr |
| Ala | Pro, Ala |
| Val | Met, Ile, Val |
| Gly | Gly |
| Ile | Ile, Met, Phe, Val, Leu |
| Phe | Met, Tyr, Ile, Leu, Phe |
| Tyr | Phe, Tyr |
| Cys | Ser, Cys |
| His | Arg, Gln, His |
| Gln | Glu, His, Gln |
| Asn | Asp, Asn |
| Lys | Arg, Lys |
| Asp | Asn, Asp |
| Glu | Gln, Glu |
| Met | Phe, Ile, Val, Leu, Met |
| Trp | Trp |

TABLE III

Most Preferred Groups of Synonymous Amino Acids

| Amino Acid | Synonymous Group |
|---|---|
| Ser | Ser |
| Arg | Arg |
| Leu | Ile, Met, Leu |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Ser, Cys |
| His | His |
| Gln | Gln |
| Asn | Asn |
| Lys | Lys |
| Asp | Asp |
| Glu | Glu |
| Met | Ile, Leu, Met |
| Trp | Trp |

Amino acid residues of the MNTF peptides and MNTF peptide analogs described herein can be naturally occurring or synthetic amino acid residues. L-and D-enantiomers of amino acid residues can be utilized in the compounds. The following abbreviations are used herein for amino acid residues: alanine (Ala, A); arginine (Arg, R); asparagine (Asn, N); aspartic acid (Asp, D); cysteine (Cys, C); glycine (Gly, G); glutamic acid (Glu, E); glutamine (Gln, Q); histidine (His, H); isoleucine (Ile, I); leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V).

Amino acid residues that are not naturally occurring and that can be present in the compounds of the invention include, beta-alanine (b-Ala) and other omega-amino acids such as 3-aminopropionic acid (Dap), 2,3-diaminopropionic acid (Dpr, Z), 4-aminobutyric acid and so forth; alpha-aminoisobutyric acid (Aib); epsilon-aminohexanoic acid (Aha); delta-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle, J); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); beta.-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); para-aminophenylalanine (Phe(pNH$_2$)); N-methyl valine (MeVal); homocysteine (hCys); 3-benzothiazol-2-yl-alanine (BztAla, B); and homoserine (hSer). Additional amino acid analogs contemplated include phosphoserine, phosphothreonine, phosphotyrosine, hydroxyproline, gamma-carboxyglutamate, hippuric acid, octahydroindole-2-carboxylic acid, statine, alpha-methyl-alanine, para-benzoyl-phenylalanine, propargylglycine, and sarcosine.

Amino acid residues that are substitutable for each other generally reside within similar classes or subclasses. As known to one of skill in the art, amino acids can be placed into different classes depending primarily upon the chemical and physical properties of the amino acid side chain. For example, some amino acids are generally considered to be hydrophilic or polar amino acids and others are considered to be hydrophobic or nonpolar amino acids. Polar amino acids include amino acids having acidic, basic or hydrophilic side chains and nonpolar amino acids include amino acids having aromatic or hydrophobic side chains. Nonpolar amino acids can be further subdivided to include, among others, aliphatic amino acids.

The cosmetic composition embodiments described herein can be obtained by conventional chemical synthesis (solid phase or solution phase synthesis), or by enzymatic synthesis from constituent amino acids or their derivatives.

Definitions

Certain terms used in the context of the describing the technology to which this disclosure pertains are set forth. Unless indicated otherwise, the following terms have the following meanings when used herein and in the appended claims.

The term "salts" herein refers to both salts of carboxyl groups and to acid addition salts of amino groups of the peptides of the invention or analogs thereof. Salts of a carboxyl group can be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid salts include, for example, salts with mineral acids such as, for example, hydrochloric acid or sulphuric acid, and salts with organic acids such as, for example, acetic acid or oxalic acid. Of course, any such salts must retain the activity of the peptides of the invention or its analogs.

"Analogs" as used in the present application includes peptides which have been modified but retain MNTF activity (e.g. by truncation, substitution, covalent attachment to another moiety, etc. relative to a 33 mer MNTF, SEQ ID NO:1). MNTF peptide analogs include, for example, esters, amides, prodrugs, and salt forms of MNTF peptides. MNTF peptide analogs include MNTF peptides that have been covalently modified by attachment to another moiety, such as for example a MNTF peptide covalently linked to a lipophilic moiety (e.g. a fatty acid), a carrier molecule, or a heterologous polypeptide to produce a fusion protein. In certain embodiments, analogs in accordance with the present disclosure include "conservative" substitutions (e.g. relative to SEQ ID NO:1). Conservative amino acid substitutions include amino acids replacements with synonymous amino acids within the same group, which have sufficiently similar physicochemical properties that substitution between members of the group will preserve the biological function of the molecule, Grantham, Science, Vol. 185, pp. 862-864 (1974). MNTF peptide analogs further encompass MNTF functional derivatives of the peptides or analogs described herein. In some embodiments, the MNTF peptide analogs include 20%, 25%, 30%, 35% or up to 40% conservative amino acid substitutions as compared with the sequence depicted in SEQ ID NO:1 or truncated versions thereof, including SEQ ID NOs:2-22.

The definition "functional derivatives" as herein used refers to derivatives which can be prepared from the functional groups present on the lateral chains of the amino acid moieties or on the terminal N- or C-groups according to known methods and are comprised in the disclosure when they are cosmetically acceptable i.e. when they do not destroy the protein activity or do not impart unacceptable toxicity to the cosmetic compositions containing them. Such derivatives includes, for example, aliphatic esters or amides of the carboxyl-groups and N-acyl derivatives of free amino groups, as well as O-acyl derivatives of free hydroxyl-groups and are formed with acyl-groups as for example alcanoyl- or aroyl-groups, prodrugs, salts of functional groups, or having a combination thereof. Functional derivatives can be produced by making covalent modifications to MNTF peptides. Covalent modifications can be introduced into a peptide by reacting targeted amino acid residues with an organic derivatizing agent that is capable of reacting with selected side chains or terminal residues. Covalent modification of polypeptides using organic derivatizing agents is well known to those of skill in the art. For example, cysteinyl residues can be reacted with alpha-haloacetates (and corresponding amines), such as chloroacetic acid or chloroacetamide, to give carboxymethyl or carboxyamidomethyl derivatives. Histidyl residues can be derivatized by reaction with diethylpyrocarbonate at pH 5.5-7.0, or with para-bromophenacyl bromide at pH 6 in 1 M sodium cacodylate. Lysinyl and amino terminal residues can be reacted with succinic or other carboxylic acid anhydrides. Arginyl residues can be modified by reaction with one or several conventional reagents, among them phenylglyoxal, 2,3-butanedione, 1,2-cyclohexanedione, and ninhydrin. Spectral labels can be introduced into tyrosyl residues by reaction with aromatic diazonium compounds or tetranitromethane; most commonly, N-acetylimidizol and tetranitromethane are used to form O-acetyl tyrosyl species and 3-nitro derivatives, respectively. Carboxyl side groups (aspartyl or glutamyl) can be selectively modified by reaction with carbodiimides (R'—N—C—N—R') such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions. Glutaminyl and asparaginyl residues can be deamidated to the corresponding glutamyl and aspartyl residues. Other modifications include hydroxylation of proline and lysine, phosphorylation of hydroxyl groups of seryl or threonyl residues, methylation of the α-amino groups of lysine, arginine, and histidine side chains (T. E. Creighton, 1983, Proteins: Structure and Molecule Properties, W.H. Freeman & Co., San Francisco, pp. 79-86), acetylation of the N-terminal amine, and, in some instances, amidation of the C-terminal carboxyl groups.

As used herein, the terms "biologically active peptide" and "biologically active fragment" refer to a peptide or polypeptide in accordance with the above description of motoneuron differentiation factors (MNDF) and/or motoneuronotrophic factors (MNTF) wherein the MNDF differentiates stem cells into motor neurons and the MNTF wherein MNTF exhibits neural protection, repair and therapeutic functions.

As used herein, the term "protein" refers to any polymer of two or more individual amino acid residues (whether or not naturally occurring) linked via peptide bonds, as occur when the carboxyl carbon atom of the carboxylic acid group bonded to the alpha-carbon of one amino acid residue is covalently bound to the amino nitrogen atom of an adjacent amino acid residue. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which are used interchangeably herein). The term "fragment" of a protein refers to a polypeptide comprising fewer than all of the amino acid residues of the protein. A "domain" of a protein is also a fragment, and comprises the amino acid residues of the protein often required to confer activity or function.

"Inhibition" means reduction in frequency, scope, degree, or persistence. Thus, when a symptom is inhibited, at least one of the frequency of occurrence of the symptom, the scope of the symptom (i.e., the geometric extent at which the symptom is exhibited on the body), the degree to which the symptom is exhibited (i.e., the severity of the symptom), and the persistence of the symptom (i.e., the duration for which the symptom is exhibited) is reduced.

As used herein, "fibrotic" diseases, disorders, or conditions include those mentioned herein, and further include acute and chronic, clinical or sub-clinical presentation, in which fibrogenic associated biology or pathology is evident. Fibrotic diseases, disorders, or conditions include diseases, disorders or conditions characterized, in whole or in part, by the excess production of fibrous material, including excess production of fibrotic material within the extracellular matrix, or the replacement of normal tissue elements by abnormal, non-functional, and/or excessive accumulation of matrix-associated components. Fibrotic diseases, disorders, or conditions include, for example, fibrogenic-related biology or pathology characterized by fibrosis. Exemplary fibrotic diseases, disorders and conditions include, for example, scleroderma (including morphea, generalized morphea, or linear scleroderma).

As used herein, "preventing" means preventing in whole or in part, or ameliorating or controlling. In certain aspects, "preventing" include inhibition or reduction of adverse dermatological effects attributable to premature skin aging.

As used herein, "subject" refers to any animal classified as a mammal, including humans, domestic and farm animals, and zoo, sports, or pet animals, such as dogs, horses, cats, sheep, pigs, cows, etc. The preferred subject is a human.

The phrase "percent (%) identity" refers to the percentage of sequence similarity found in a comparison of two or more sequences. Percent identity can be determined electronically using any suitable bioinformatics software (for example, BLAST). Likewise, "similarity" between two sequences (or one or more portions of either or both of them) is determined by comparing the sequence of one sequence to a second sequence. As described herein, the terms "homology and homologues" refer to peptides having amino acid sequence homologies to the protein sequence of interest. Such peptide typically has at least about 70% homology, and can be at least about 80%, 90%, 95%, 97% or 99% homology with the relevant sequence, for example over a region of at least about 15, 20, 30, 40, 50, 100 more contiguous amino acid/polypeptide of the homologous sequence. They may further comprise up to about 25%, 30%, 40% or 50% conservative amino acid changes relative to a reference sequence (e.g. SEQ ID NO:1), depending on the length of the peptide and the reference sequence.

Methods of Making MNTF Peptides And Analogs Thereof

The method used to make the MNTF Peptides described herein is not critical. Substantially any known method of peptide synthesis can be used, as can methods hereafter developed. As those of skill familiar with the art and the disclosure will appreciate, sequences comprising the MNTF active domain and peptide analogs thereof can impart neural protection, repair and therapeutic functions on motorneurons in vitro and in vivo. The MNTF factors described herein can be produced synthetically or recombinantly, or isolated from native cells.

It will be appreciated by those of skill that the precise chemical structure of peptides comprising the various MNTF peptides or analogs thereof will vary depending upon a number of factors. For example, a given polypeptide can be obtained as an acidic or basic salt, or in neutral form, since ionizable carboxyl and amino groups are found in the molecule.

The peptides of the present disclosure can be prepared by any well known procedure in the art, such as solid phase synthesis or liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their alpha-amino groups and side chain functional groups protected with appropriate protective groups are condensed one by one in order from the C-terminus to the N-terminus, and one where the amino acids bound to the resin or the protective group of the α-amino groups of the peptides are released, the peptide chain is thus extended in this manner. Solid phase synthesis methods are largely classified by the tBoc method and the Fmoc method, depending on the type of protective group used.

Typically used protective groups include tboc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and $Cl_2$-Bzl (2,6dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups).

It is understood that an MNTF peptide composition of the present disclosure can be made by a method that is well known in the art, including but not limited to chemical synthesis by solid phase synthesis and purification away from the other products of the chemical reactions by HPLC, or production by the expression of a nucleic acid sequence (e.g., a DNA sequence) encoding a peptide or polypeptide comprising an MNTF peptide described herein in an in vitro translation system or in a living cell. The MNTF peptide of the composition can be isolated and extensively dialyzed to remove one or more undesired small molecular weight molecules and/or lyophilized for more ready formulation into a desired vehicle. It is further understood that additional amino acids, mutations, chemical modification and such like, if any, that are made in a MNTF peptide component should not substantially interfere with receptor recognition of the MNTF docking sequence.

After synthesis of the desired peptide, it is subjected to the de-protection reaction and cut out from the solid support. Such peptide cutting reaction can be carried with hydrogen fluoride or trifluoromethane sulfonic acid for the Boc method, and with TFA for the Fmoc method.

The crude peptide thus obtained is then subjected to purification. Purification is carried out by any one of the methods known for this purpose, i.e. any conventional procedure involving extraction, precipitation, chromatography, electrophoresis, or the like. For example, HPLC (high performance liquid chromatography) can be used. The elution can be carried using a water-acetonitrile-based solvent commonly employed for protein purification.

A peptide or polypeptide corresponding to one or more fragments of MNTF can be at least two amino acid residues in length, and can contain up to 2, 3, 4, 5, 6, 7, 8, 9, 10, 11, 12, 13, about 15, about 20 or about 30 amino acid residues or so, and a functional derivatization, e.g. a palmitylation. Preferably, the MNTF peptide or analog thereofs described herein include not more than the 33 amino acid residues of SEQ ID NO: 1. Suitable peptides includes 32 consecutive amino acid residues of SEQ ID NO: 1, 31 consecutive amino acid residues, 30 consecutive amino acid residues, and so on, down to peptides as small as dipeptides. It is important that in preferred embodiments the MNTF peptides and analogs thereof include the phenylalanine and serine residues at positions 17 and 18 of SEQ ID NO: 1.

The MNTF peptides and analogs thereof described herein can be used in assays and kits for assays, either in the free form or linked to a carrier molecule such as a protein or a solid particle, as well as modified peptides linked to a label or tracer, such as biotin or fluorescein isothiocyanate.

Crosslinking of MNTF peptide fragment to a water-insoluble support matrix can be performed with bifunctional agents well known in the art including 1,1 bis(diazoacetyl) 2 phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Bifunctional agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates can be employed for protein immobilization.

Crosslinking of an MNTF peptide fragment to a second protein, including a second MNTF1 peptide fragment, can be performed using the bifunctional reagents described herein. In another alternative, there is inserted a spacer, for example a dithiol group or a diamino group or multiples of amino acid residues, e.g. glycine. The spacer can also be a homo- or heterobifunctional crosslinker, for example the heterobifunctional crosslinker N-(4-carboxy-cyclohexyl-methyl)-maleimide.

Cosmetic And Dermatologic Compositions

Compositions for use as described herein can comprise one or more of the MNTF peptides or analogs together with one or more suitable diluents, carriers, and other relatively inert ingredients. Such compositions includes any of the variety of preservatives, solvents, binding agents, emulsion stabilizers, film formers, anti-caking agents, moisturizers, and other ingredients commonly used in cosmetic creams, dermatologic products, and other topically-applied products. A tremendous variety of such ingredients are known in the art.

The cosmetic formulations of the present invention includes cosmetically acceptable carriers, diluents, solubilizing or emulsifying agents, and salts of the type that are available in the art. Examples of suitable agents that can be included in a cosmetic composition, include cosmetically acceptable carriers, thickeners, diluents, buffers, preservatives, surface active agents, neutral or cationic lipids, lipid complexes, liposomes, penetration enhancers, carrier compounds and other cosmetically acceptable carriers or excipients and the like, in addition to the MNTF peptides described herein.

Numerous types of penetration enhancers are known, such as fatty acids, bile salts, chelating agents, surfactants and non-surfactants (Lee et al., Critical Reviews in Therapeutic Drug Carrier Systems 8, 91-192 (1991); Muranishi, Critical Reviews in Therapeutic Drug Carrier Systems 7, 1-33 (1990)). One or more penetration enhancers can be included in the compositions described herein.

Various fatty acids and their derivatives which act as penetration enhancers include, for example, cabrylic acid, oleic acid, lauric acid, capric acid, caprylic acid, hexanoic acid, myristic acid, palmitic acid, valeric acid, stearic acid, linoleic acid, linolenic acid, arachidonic acid, oleic acid, elaidic acid, erucic acid, nervonic acid, dicaprate, tricaprate, recinleate, monoolein (a k.a. 1-monooleoyl-rac-glycerol), dilaurin, arachidonic acid, glyceryl 1-monocaprate, 1-dodecylazacycloheptan-2-one, acylcarnitines, acylcholines, mono- and diglycerides and physiologically acceptable salts thereof (i.e., oleate, laurate, caprate, myristate, palmitate, stearate, linoleate, etc.). Lee et al., Critical Reviews in Therapeutic Drug Carrier Systems page 92 (1991); Muranishi, Critical Reviews in Therapeutic Drug Carrier Systems 7, 1 (1990); El-Hariri et al., J. Pharm. Pharmacol. 44, 651-654 (1992)).

In certain embodiments, exemplary MNTF peptides and analogs thereof includes N-terminal modification by fatty acids and/or alkylcarbonyl (Alk-C(O)-) of from 2 to about 22 carbon atoms, or a protecting group selected from the group consisting of benzyloxycarbonyl, tert-butyloxycarbonyl, fluorenyl-methoxycarbonyl and allyloxycarbonyl, and Y is OH or $NH_2$ and salts thereof. In certain other embodiments, the alkylcarbonyl contain 10 to 20, 12 to 18, 2 to 22, for example 6, 8, 10, 12, 14, or 16 carbons. In one particular embodiment, suitable N-terminal modification on the MNTF peptide or analog is by palmitylation (e.g. palmitic acid).

The compositions described herein can be administered topically in any of a variety of forms.

Formulations for topical administration includes dermal patches, ointments, lotions, serums, creams, gels, drops, sprays, liquids and powders. Conventional cosmetic carriers, aqueous, powder or oily bases, thickeners and the like can be used.

As used herein, formulation of the MNTF peptides and analogs described herein for cosmetic, skincare, and/or dermatological applications includes, for example, known anti-wrinkle active ingredients, including for example, flavone glycosides (e.g. alpha-glycosylrutin), coenzyme $Q_{10}$, vitamin E and derivatives and the like, as well as known sunblock ingredients, moisturizers, and perfume.

The MNTF peptide- or analog-containing compositions described herein can be administered for "cosmetic" or "skincare" (i.e., dermatologic) applications, either alone or as an "additive" in combination with other suitable agents or ingredients. As used herein, "cosmetic" and "skincare" applications includes, for example, preventive and/or restorative applications in connection with dermatological changes in the skin, such as, for example, during pre-mature skin aging; dryness; roughness; formation of dryness wrinkles; itching; reduced refatting (e.g. after washing); visible vascular dilations (e.g. telangiectases, cuperosis); flaccidity; formation of wrinkles and lines; local hyperpigmentation; hypopigmentation; incorrect pigmentation (e.g. age spots); increased susceptibility to mechanical stress (e.g. cracking) and the like); skin-sagging (e.g. lack of firmness) and the appearance of dry or rough skin surface features.

The MNTF peptides and analogs described herein can be formulated as dermapharmaceutical formulations for topical administration to counter any dermatological disease, disorders, or conditions characterized in whole or in part by abnormal scarring, hypertrophic scarring, burns, skin trauma, keloid, psoriasis, skin diseases, systemic diseases, lesions, tumors and cancers, acne/follicular diseases, eczema, dermatitis and allergies, blistering diseases, immunological skin disorders, scaly skin diseases, erosions and ulcers, vascular skin problems, pigmentation problems, excessive pruritus (itch), local skin reactions to external agents, and deep skin disorders and fibrotic conditions. In other embodiments, the method of the present disclosure can be used to minimize or prevent scar formation, such as hypertrophic scars, keloids and excessive burn scarring, atrophic scars, and widespread scars, in humans or other mammals, particularly those individuals prone to excessive scarring.

The MNTF peptides and analogs thereof described herein can be formulated as dermapharmaceutical formulations for topical administration by a variety of methods. An examples of such a method includes encapsulating appropriate amount of an MNTF peptide or analog in a vector selected from the group consisting of macro-capsules, micro-capsules, nano-capsules, liposomes, chylomicrons and microsponges. Another example of such a method includes absorbing an MNTF peptide or analog on a material selected from the group consisting of powdered organic polymers, talcs, bentonites, and other mineral supports. A third example of such a method includes mix the MNTF peptide or analog with other ingredients selected from a group comprising extracted lipids, vegetable extracts, liposoluble active principles, hydrosoluble active principles, anhydrous gels, emulsifying polymers, tensioactive polymers, synthetic lipids, gelifying polymers, tissue extracts, marine extracts, Vitamin A, Vitamin C, Vitamin D, Vitamin E, solar filters, and antioxidants. Other examples of suitable compositions can be found, for example, in US Patent application publication number 2005/0249720.

The MNTF peptides and analogs described herein can be incorporated into any gelanic form, such as O/W emulsions and W/O emulsions, milks, lotions, gelifying and thickening, tensioactive and emulsifying polymers, pomades, lotions, capillaries, shampoos, soaps, powders, sticks and pencils, sprays, body oils.

Regardless of the method by which compounds described herein are administered to a patient, colloidal dispersion systems can be used as delivery vehicles to enhance the in vivo stability of the peptides and/or to target the peptides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:peptide complexes of uncharacterized structure. An example of a colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 6, 698-708 (1995)). Sustained-release dosage forms of the compounds described herein can be used.

Dosing And Administration

The precise amount of the MNTF peptide or analog administered to a subject is not critical, except that it should be a sufficient amount to effect improvement of the condition for which the composition containing the peptide or analog is administered. Dosing can be dependent on a number of factors, including severity and responsiveness of the condition to be treated, and with the course of treatment lasting from several days to several months, or until improvement of a condition is effected or a diminution of a symptom is achieved.

By way of example, MNTF peptides and analogs can be administered to achieve from about 0.01 micrograms per milliliter (μg/mL) to about 10 milligrams per milliliter, from about 0.1 μg/mL to about 500 μg/mL, from about 0.1 μg/mL to about 1500 μg/mL, from about 1 μg/mL to about 2000 μg/mL, and from about 0.1 μg/mL to about 5000 μg/mL, including any range within these ranges, final concentrations at a target site. Compositions that include the peptide or analog in a concentration in one or more of these ranges are appropriate. Similarly, appropriate dosage values can be estimated based on the experimental data provided herein.

Appropriate dosage values can depend on the characteristics of the site to which the composition is to be administered and on the form of the peptide. By way of example, palmitylated MNTF peptide analogs are much less water soluble than the corresponding non-palmitylated MNTF peptides. For example, the water solubility of the palmitylated hexamer having the amino acid sequence SEQ ID NO: 2 is on the order of one milligram per milliliter. A gel containing approximately one milligram per milliliter of that peptide analog can be diluted about twenty-fold to produce a product suitable for daily topical use by a human, the product containing about 50 micrograms of the peptide per milliliter.

Guidance as to particular dosages and methods of delivery is provided in the literature and generally available to practitioners in the art. Those skilled in the art will employ different formulations for nucleotides than for proteins or their inhibitors. Persons of ordinary skill in the art can easily estimate repetition rates for dosing based on measured residence times and concentrations of the drug in bodily fluids or tissues. Following successful treatment, it can be desirable to have the patient undergo maintenance therapy to prevent the recurrence of the disease state, wherein a selected compound is administered in maintenance doses, ranging from 0.01 mg/kg to 100 mg per kg of body weight, once or more daily, to once every 20 years. In the treatment or prevention of certain conditions, an appropriate dosage level will generally be about 0.001 to 100 mg per kg patient body weight per day which can be administered in single or multiple doses. A suitable dosage level can be about 1 to about 40 mg/kg per day. In certain embodiments, compounds provided herein, including MNTF peptides and MNTF peptide analogs, are administered in an amount to achieve in vivo concentrations from about 1 micromolar to about 10 millimolar, from about 10 micromolar to about 5000 micromolar, or from about 30 micromolar to about 3000 micromolar, and from about 25 micromolar to about 3000 micromolar final concentration over the damaged site, and including, about 25 micromolar, or about 1600 micromolar, or about 3000 micromolar final concentration over the damaged site, and still more typically between about 1 micromolar to about 1000 micromolar.

The invention can be appreciated in certain aspects with reference to the following examples, offered by way of illustration, not by way of limitation. Materials, reagents and the like to which reference is made in the following examples are obtainable from commercial sources, unless otherwise noted.

EXAMPLES

Example 1

Manufacturing Method And Covalent Attachment of Fatty Acids MNTF Peptides

The ingredient is synthesized by solid phase synthesis method well established for peptide manufacturing described by Merrifield. The α-amino group of each amino acid is protected with Fmoc groups. Side chain functional groups are also blocked with various appropriate protective groups. The peptide chain is formed by derivatization of the c-terminal amino acid onto the resin. The protective groups were removed (de-blocking step), and coupling with each amino acid in the sequence. The completion of each coupling was monitored by the Ninhydrin (NIN) test. The addition/coupling process is performed for each amino acid through out the peptide chain. When the full peptide sequence was completed, the peptide resin was thoroughly rinsed and dried. The peptide is then cleaved from the Peptide Resin. The crude peptide was checked for purity by RP-HPLC. When the crude peptide had met the required minimum purity criteria, it was submitted for purification by preparative RP-HPLC purification. Those fractions that met the final purity criteria (>95%) were pooled and sent for lyophilization.

The lyophilized hexapeptide is conjugated with a palmitoyl derivative to produce palmitoyl hexapeptide according to the protocol described in Rijkers, D. T. S., et al., Tetrahedron Letters 46 (19):3341-3345 (2005). This method utilizes a convenient solid phase synthesis of S-palmitoyl transmembrane peptides. The highly acid labile S-(4-methoxytrityl) group is preferred over the S-(tert-butylsulfanyl) group for protection of the cysteine side chain since the latter gives rise to quantitative desulfurization during on-resin deprotection. The resulting free thiol function is modified with palmitic acid via a carbodiimide-mediated coupling and the title compounds are obtained in good yields and purity. The palmitoyl hexapeptide is sent for ion exchange to convert to acetate salt by preparative RP-HPLC.

Using the procedure described in Rijkers, D. T. S., et al., MNTF peptides having SEQ ID NOS:2-27 are conjugated to fatty acids having 5, 6, 8, 10, 12, 14 and 16 carbons as well as fatty acids having alternative numbers of carbons. Fatty acids that are conjugated to MNTF peptides and analogs thereof are selected from the following cabrylic acid, oleic acid, lauric acid, capric acid, caprylic acid, hexanoic acid, myristic acid, palmitic acid, valeric acid, stearic acid, linoleic acid, linolenic acid, arachidonic acid, oleic acid, elaidic acid, erucic acid, and nervonic acid. The MNTF peptides or analogs thereof formed by covalent attachment to these fatty acids, as well as others, are then tested for their ability to be used in topical formulations that facilitate skin penetration.

Example 2

The following is an example of a cosmetic formulation of an MNTF peptide (Palmitylated MNTF peptide analog), made in the form of a topical anhydrous gel.

| Topical anhydrous gel | % w/w |
| --- | --- |
| Glycerine | 37.91 |
| Butylated Hydroxtoluene (BHT) | 0.11 |
| Diethylene glycol monoethyl ether (DGME) | 46.98 |
| Lauryl lactate (LL) | 5.01 |
| Germaben II | 0.34 |
| Diazolidinyl urea | 0.10 |
| Methyl paraben | 0.01 |
| Propylparaben | 0.01 |
| Propylene Glycol (PG) | 0.19 |
| Pal-hexapeptide (Pal-FSRYAR; SEQ ID NO: 2) | 0.10 |
| $SiO_2$ | 5-9 |
| Total | 100.00 |

Example 3

The following is an example of a cosmetic formulation of a palmitylated MNTF peptide analog, made in the form of a hydroalcoholic gel.

| Hydroalcoholic gel | % w/w |
| --- | --- |
| Ethanol, 190 proof | 68.86 |
| Water | 24.12 |
| Chrystaphyl 98 ™ (lauryl acetate) | 5.00 |
| Carbopol 980 | 1.00 |
| Pal-hexapeptide (Pal-FSRYAR; SEQ ID NO: 2) | 1.00 |
| Total | 100.00 |

Example 4

The following is an example of a cosmetic formulation of palmitylated MNTF peptide analog, made in the form of a cream.

| Cream | % w/w |
| --- | --- |
| Dermabase ™ Cream | 88.90 |
| Purified water (~55%) | |
| Mineral oil | |
| Petrolatum | |
| Cetostearyl alcohol | |
| Sodium lauryl sulfate | |
| Isopropyl palmitate | |
| Propylene Glycol | |
| Imidazolidinyl urea | |
| Methylparaben | |
| Propylparaben | |
| Water | 5.00 |
| Chrystaphyl 98 ™ (lauryl lactate) | 5.00 |

-continued

| Cream | % w/w |
| --- | --- |
| Butylated hydroxyanisole | 0.10 |
| Pal-hexapeptide (Pal-FSRYAR; SEQ ID NO: 2) | 1.00 |
| Total | 100.00 |

Example 5

Measurement of Inhibition of Nitric Oxide Production As A Model For Inhibition of Inflammation Method The study method chosen is similar to that published in the reference Tsai et al. (Tsai et al, Inhibition of inflammatory nitric oxide production and epidermis damages by Saccharomycopsis Ferment Filtrate. J Dermatol Sci 2006 June 42 (3): 249-57. Laskin, Multifunctional Role of Nitric Oxide in Inflammation, Trends Endocrinol Metab 1994; 5:377-382. Lyons, Emerging Roiles of Nitric Oxide in Inflammation, Hospital Practice, Jul. 15, 1996: 69-86.)

The objective of the study was to investigate the inhibition effect of Pal-hexapeptide (SEQ ID NO: 2, in palmitylated form) on gamma interferon-induced NO production in epidermal keratinocytes in culture.

Experimental Summary

Anti-inflammatory effect was observed as a reduction of nitric oxide production in keratinocytes. Keratinocytes were incubated 48 hours with gamma-interferon (300 U/ml) alone (as control) or with gamma-interferon together with different concentrations (0.1 µM, 1 µM, 10 µM, 100 µM and 1000 µM) of Pal-hexapeptide. Gamma interferon plus aminoguanidine (10 mg/mL) was used as positive control. The amount of NO production was detected by Griess reaction. Nitric oxide readily oxides to nitrite in aqueous medium, and this reaction was measured as nitrite accumulation in the medium. Following a 15 minute incubation at room temperature, derivatization of the nitrite present resulted in formation of a chromophore with an absorbance maximum at 542 nanometers. The optical density of the wells were read using a Tibertek Mutiskan (MCC microplate reader at a wavelength of 540 nm, subtracting the absorbance at a reference wavelength of 620 nm.) A printout of the absorbance values was generated by the plate reader, and data were entered into an EXCEL spreadsheet for analysis. The average absorbance and standard deviations were expressed as percent of control absorbances.

Figure 2A:
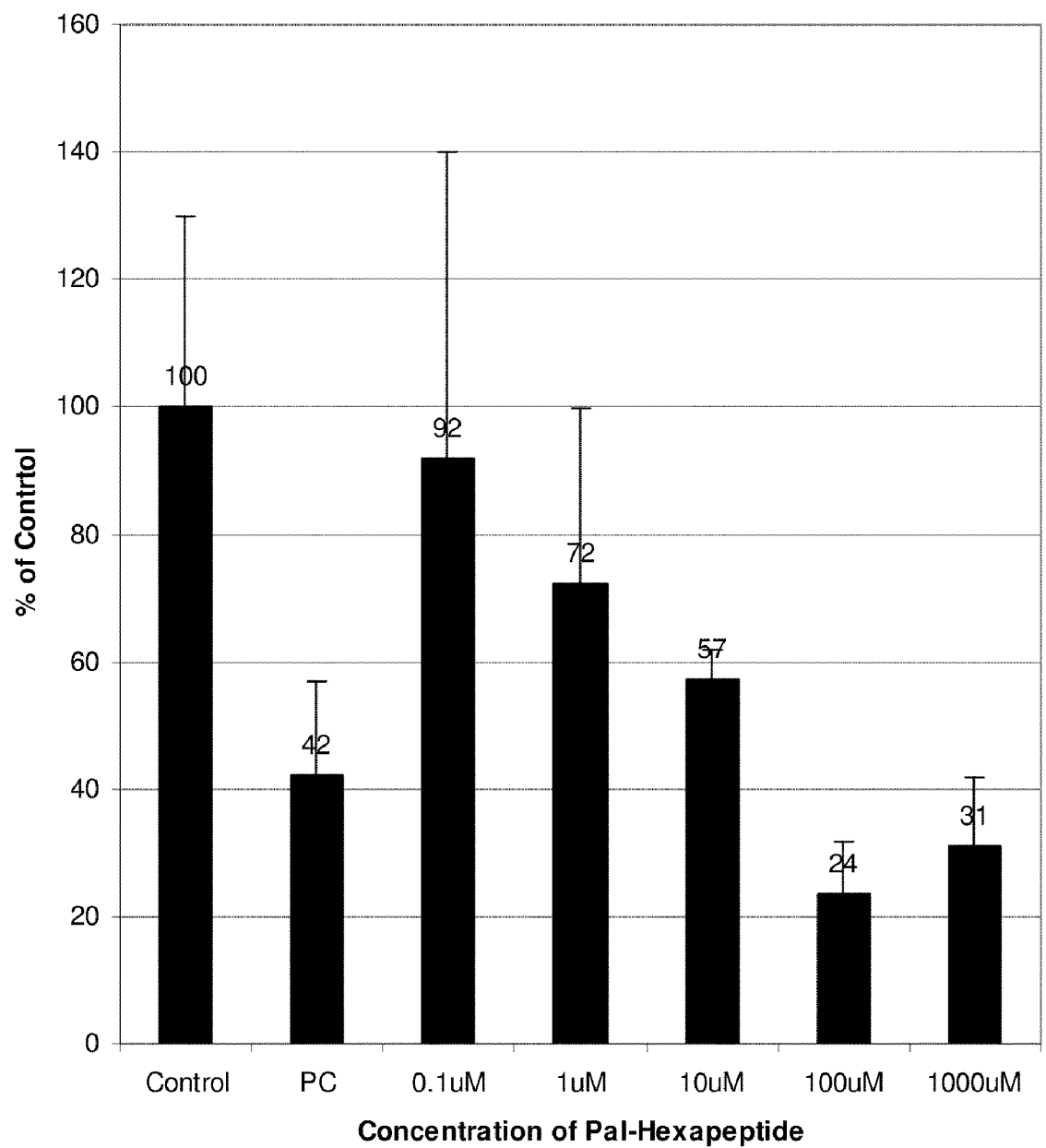
FIG. 2A is a bar graph that illustrates dose-response data showing the effect of an MNTF molecule (Pal-Hexapeptide) described herein on inhibition/reduction of gamma interferon-dependent nitric oxide production (i.e., an indicator of inflammation) in keratinocytes.

As shown in FIG. 2A, in the presence of Pal-hexapeptide (palmitylated peptide having the sequence; SEQ ID NO: 2) at 0.1 µM, 1 µM, 10 µM, 100 µM and 1000 µM, the nitric oxide production induced by Gamma-interferon were 92%, 72%, 57%, 24% and 31% of the control respectively. Under the same conditions, the positive control (Gamma interferon+ AG) reduced the nitric oxide production to 42% of the control level. The nitric oxide production was reduced in a dose dependent manner by Pal-hexapeptide, which indicates that the compound is able to inhibit inflammation. The reduction of nitric oxide production by 100 µM and 1000 µM Pal-hexapeptide are statistically significant. This study provided the evidence to indicate the beneficial effects of Pal-hexapeptide in preventing nitric oxide production in keratinocytes and the potential of anti-inflammation effects on the skin.

Figure 2B:
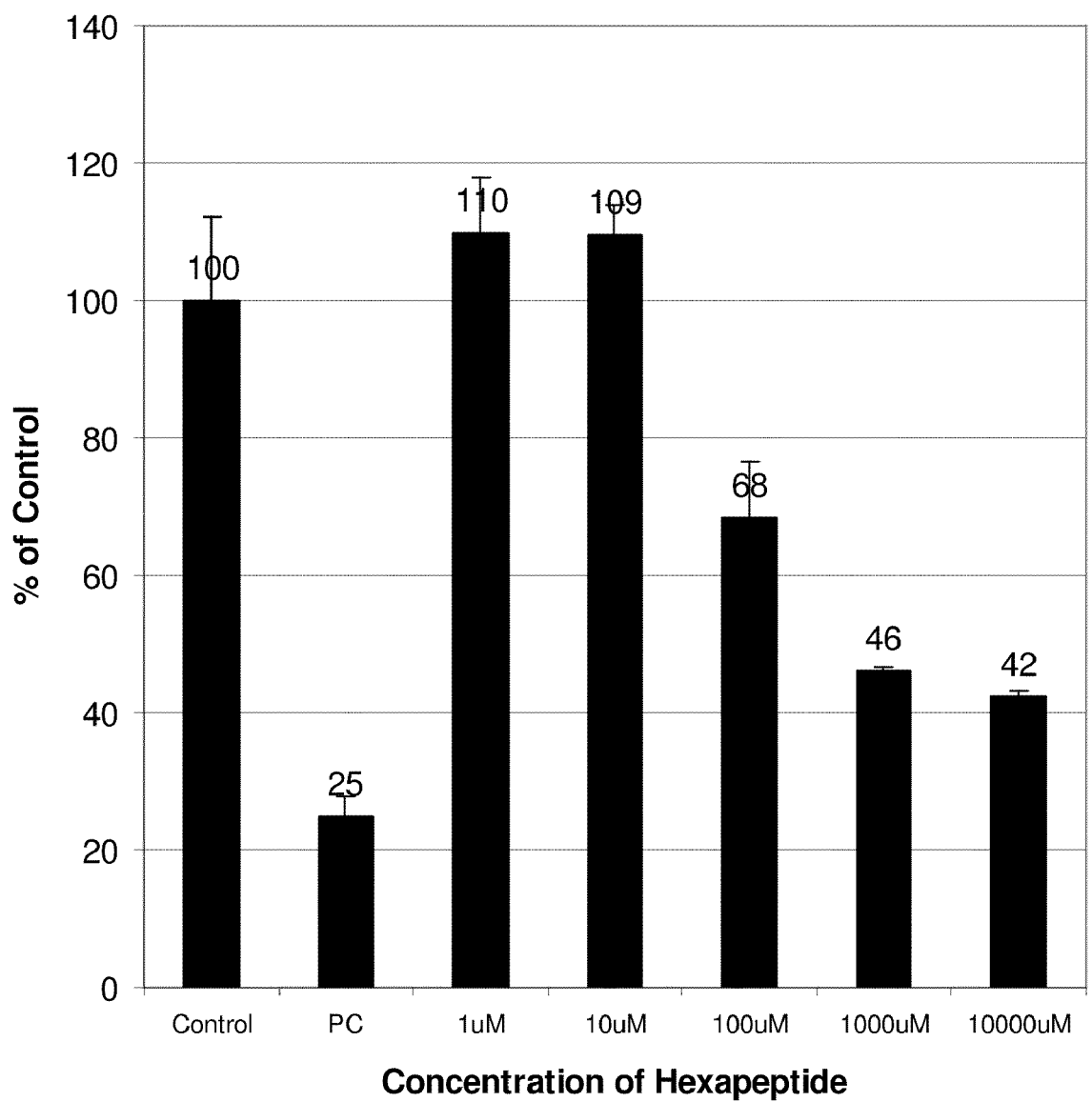
FIG. 2B is a bar graph that shows reduction of nitric oxide production in keratinocytes by an MNTF hexapeptide described herein.

As shown in FIG. 2B, in the presence of hexapeptide at 100 µM, 1,000 µM and 10,000 µM, the nitric oxide production induced by Gamma-interferon were 68%, 46%, and 42% of control in a dose dependent manner and statistically significant, while the positive control reduced NO production to 25% of control.

Example 6

Lipid Peroxide Assay

Determination of the Effect of Pal-Hexapeptide On Cellular Peroxide Levels In Human Epidermal Keratinocytes Using A Peroxide-Specific (Fluorescent) Dye And Flow Cytometry Method Hydrogen peroxide can induce damages to skin cells. The dermal protective efficacy of Pal-hexapeptide was assessed by measuring basal peroxide levels in the presence and absence of the compound.

Basal peroxide production, generated by normal cellular metabolism, induce gradual development of low levels of peroxide-specific cellular fluorescence.

Extracellular peroxides (e.g., $H_2O_2$ added exogenously) can permeate the cell membrane and cause a rapid and dramatic increase in the peroxide-specific fluorescence of the cell. Cellular peroxides levels can be measured by flow cytometry using the peroxide-specific dye, 2',7'-dichlorofluorescein diacetate (DCFH-DA). DCFH-DA is initially non-fluorescent and is rapidly concentrated within living cells by an enzyme-dependent process. Following modification by cellular peroxides, this dye exhibits an intense green fluorescence when excited by laser light. The results of the assay indicates if a test compound functions as an oxidant or an anti-oxidant in a cellular system. If the test article functions as an anti-oxidant, this assay can also be used to determine if the test compound can permeate the cell membrane to quench intracellular peroxide or if it can only affect extracellular peroxide levels (Bass et al., 1983, J. Immunol. 130:1910-1917; Bombick et al., 1992, Toxicol. Meth. 2:255-264).

Experimental Summary

Human primary keratinocytes, generally on the third passage, were seeded in T75 flasks and cultured until 70-80% confluent. A cell suspension was created and these cells were loaded with the dye DCFH-DA. The pre-incubated cells were exposed to dilutions of the Pal-hexapeptide having the amino acid sequence SEQ ID NO: 2 in two triplicate sets per dilution. One triplicate set was incubated with $H_2O_2$ (exogenous source of peroxide), and both sets were stained with Propidium Iodide. Cell viability and peroxide production were determined by fluorescence readings on a FACScan flow cytometer. Peroxide value increases or decreases of 25% or more compared to vehicle control values are considered biologically significant.

Figure 3A:
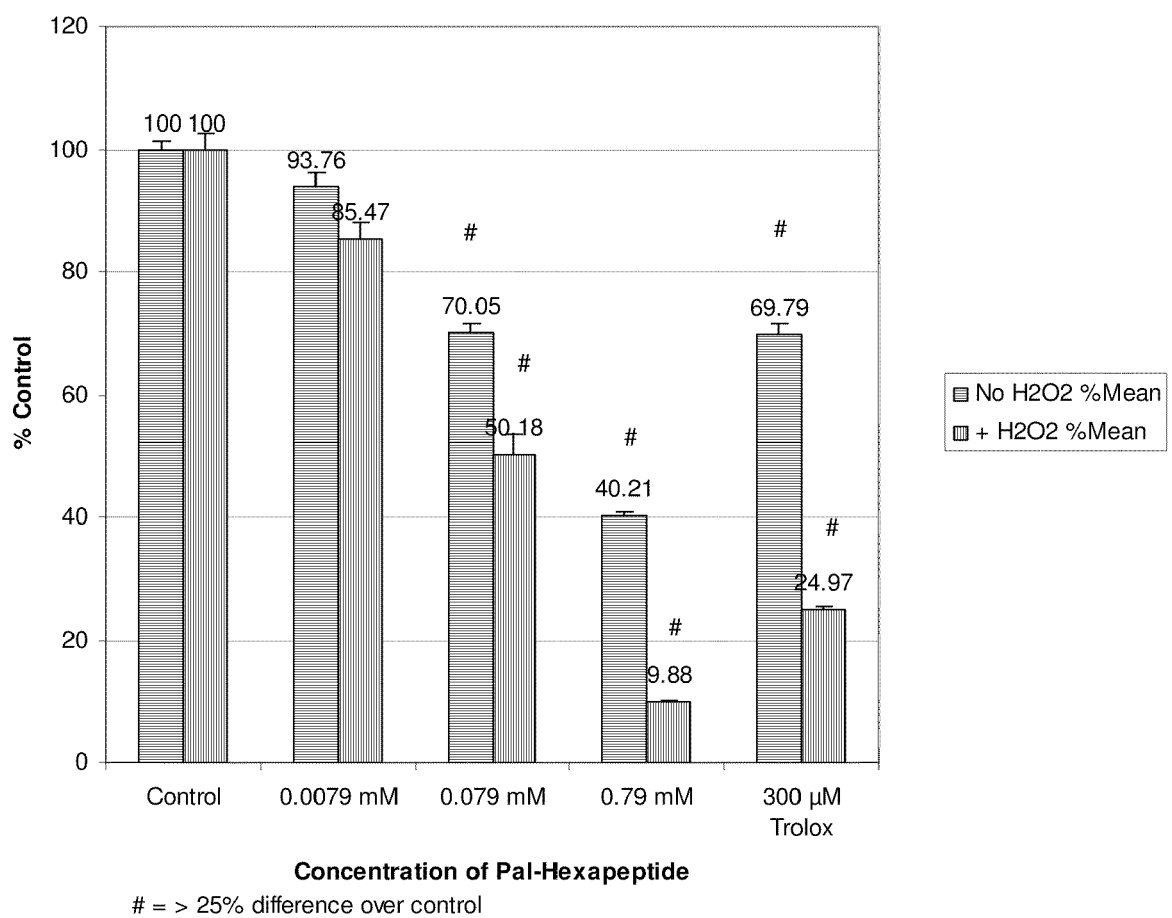
FIG. 3A is a bar graph that illustrates the dose-response data showing the effect of an MNTF molecule (Pal-Hexapeptide) described herein on inhibition/reduction of endogenous and exogenous cellular peroxide levels (i.e., an indicator of anti-oxidative capacity).

The effects of Pal-hexapeptide on cellular peroxide levels were assessed as follows. In the endogenous peroxide assay without exogenous $H_2O_2$ (i.e., endogenous peroxide production by keratinocytes themselves), with Pal-hexapeptide at 0.079 mM, and 0.79 mM the peroxide level was reduced to 70.05% and 40.21% of the control respectively, as shown in FIG. 3A and Table 1. The positive control 300 µM Trolox reduced the peroxide level to 69.79%. In the assay with exogenous added peroxide (i.e. peroxide production by keratinocytes and exogenous $H_2O_2$), at 0.079 mM and 0.79 mM, the peroxide levels were 50.18% and 9.88% of the control respectively. The positive control 300 µM Trolox reduced the peroxide level to 24.97%. Cell viability, expressed as % of non-viable, was about the same for cells treated with and cells not treated with Pal-hexapeptide. The reduction of peroxide production by Pal-hexapeptide in a dose dependent manner is biologically significant and also highly statistically significant. These data demonstrate that the peptide is able to affect cellular peroxide levels.

Figure 3B:
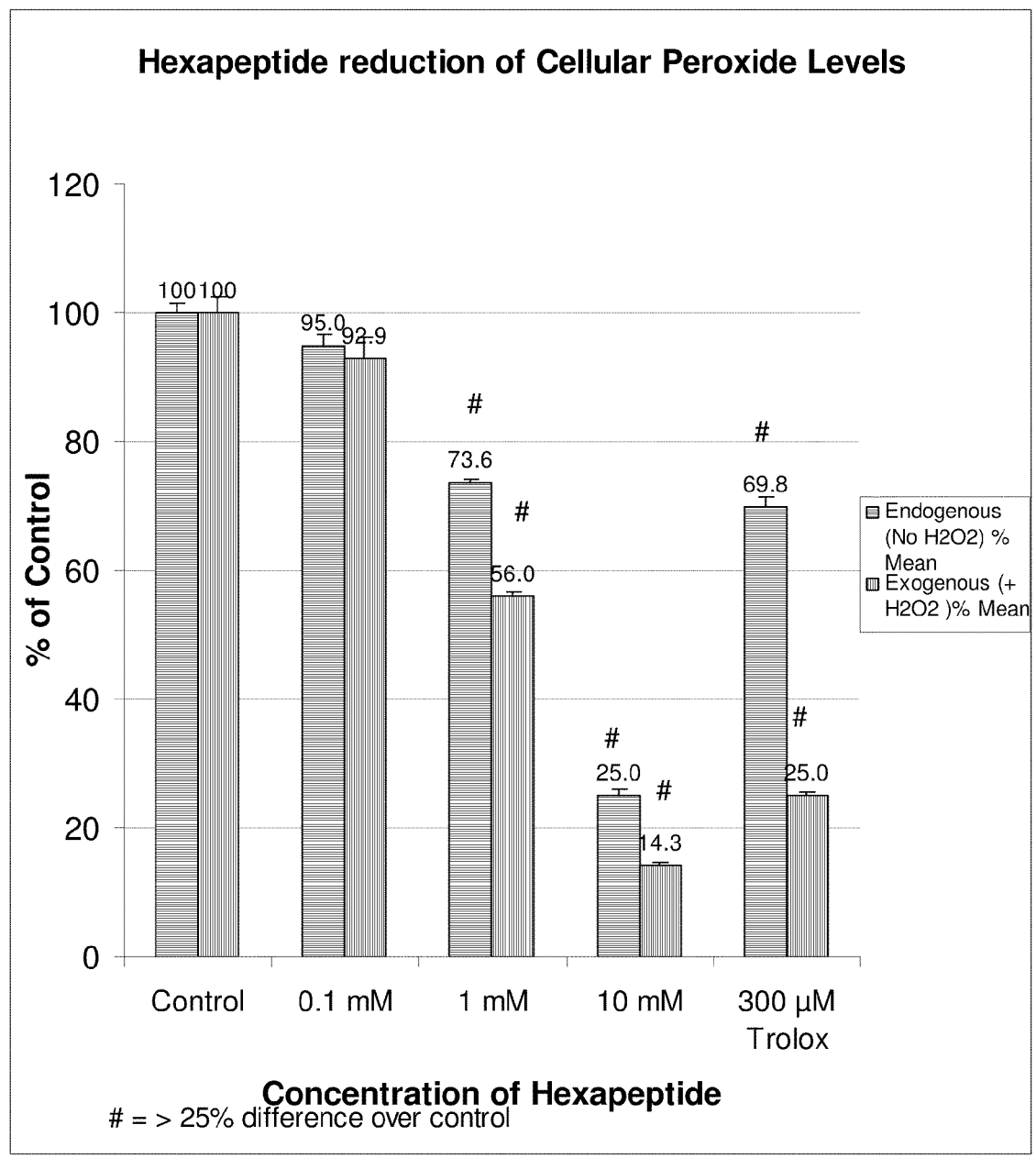
FIG. 3B is a bar graph that illustrates the reduction of the endogenous and exogenous cellular peroxide levels by an MNTF hexapeptide described herein.

The effects of the hexapeptide on cellular peroxide levels were as follows. In the endogenous peroxide assay without exogenous $H_2O_2$ (i.e., endogenous peroxide production by keratinocytes themselves), with hexapeptide at 1 mM, and 10 mM the peroxide level was reduced to 73.57% and 25.02% of the control respectively, as shown in FIG. 3B and Table 1. The positive control 300 µM Trolox reduced the peroxide level to 69.79%. In the assay with exogenous added peroxide (i.e. peroxide production by keratinocytes and exogenous $H_2O_2$), 1 mM and 010 mM, the peroxide levels were 56.00% and 14.29% of the control respectively. The positive control 300 µM Trolox reduced the peroxide level to 24.97%. Cell viability, expressed as % of non-viable, was about the same for cells treated and not treated with hexapeptide. The reduction of peroxide production by hexapeptide in a dose dependent manner is biologically significant and also highly statistically significant. These data demonstrate that the peptide is able to affect cellular peroxide levels and thereby reduce or inhibit photodamage associated inflammation or free radical damage in a skin cell.

TABLE 1

Summary of Peroxide Levels (6-mer)

| Test article | Conc. | % Control (no $H_2O_2$) | >25% Increase or Decrease in Peroxide Level | % Control (with $H_2O_2$) | >25% Increase or Decrease in Peroxide Level |
|---|---|---|---|---|---|
| GM602, | 0.1 mM | 94.9 | — | 92.9 | — |
| Lot #332614 | 1 mM | 73.6 | Decrease | 56.0 | Decrease |
| (6 mer) | 10 mM | 25.0 | Decrease | 14.3 | Decrease |
| Pal 6 mer | 0.00079 mM | 93.8 | — | 85.5 | — |
| | 0.0079 mM | 70.1 | Decrease | 50.2 | Decrease |
| | 0.079 mM | 40.2 | Decrease | 9.9 | Decrease |

"—" = neither increase nor decrease in peroxide level

Tables 2-4 illustrate the efficacy data for the exemplary 3,4, and 5 mer MNTF in anti-oxidation on human skin cells. The MNTF 3 mer (SEQ ID NO:9) decreased both endogenous and exogenous peroxide levels at concentrations of 1 mM and 10 mM in a dose-dependent manner. The MNTF 4 mer (SEQ ID NO:11) decreased both endogenous and exogenous peroxide levels at 10 mM, but only decreased the exogenous peroxide level (as defined by the 25% cutoff) at 1 mM. The MNTF 5 mer (SEQ ID NO:17) decreased both endogenous and exogenous peroxide levels at 1 and 10 mM in a dose-dependent manner. The Pal 3 mer. Pal 4 mer, and Pal 5 mer, as a 1 mM concentration in DPBS, decreased exogenous peroxide levels.

TABLE 2

Summary of Peroxide Levels (3-mer)

| Test article | Conc. | % Control (no $H_2O_2$) | >25% Increase or Decrease in Peroxide Level | % Control (with $H_2O_2$) | >25% Increase or Decrease in Peroxide Level |
|---|---|---|---|---|---|
| CS2307, | 0.1 mM | 98.7 | — | 95.5 | — |
| Lot #E040 | 1 mM | 60.6 | Decrease | 62.5 | Decrease |
| (3 mer) | 10 mM | −8.5 | Decrease | −1.5 | Decrease |
| Pal 3 mer | 0.01 mM | 99.4 | — | 101.0 | — |
| | 0.1 mM | 98.7 | — | 96.1 | — |
| | 1 mM | 101.1 | — | 71.9 | Decrease |

"—" = neither increase nor decrease in peroxide level

Conclusion: In experiments where administration of the exemplary MNTF 3-mer (SEQ ID NO:9) was given at a concentration of 1 mM, endogenous peroxide level was reduced to 60.6% compared to that of the control and exogenous peroxide level was reduced to 62.5% of control. At a concentration of 10 mM, endogenous peroxide level was reduced to 0, and exogenous peroxide level was reduced to 0%. Thus, in this exemplary analysis, the test article comprising an exemplary 3-mer MNTF molecule, decreased both endogenous and exogenous peroxide levels from at 1 and 10 mM in a dose-dependent manner.

TABLE 3

Summary of Peroxide Levels (4-mer)

| Test Article | Conc. | % Control (no $H_2O_2$) | >25% Increase or Decrease in Peroxide Level | % Control (with $H_2O_2$) | >25% Increase or Decrease in Peroxide Level |
|---|---|---|---|---|---|
| CS2308, | 0.1 mM | 98.6 | — | 84.5 | — |
| Lot #D266 | 1 mM | 77.2 | — | 54.9 | Decrease |
| Exemplary 4mer | 10 mM | 25.2 | Decrease | −5.8 | Decrease |
| Pal 4mer | 0.01 mM | 97.2 | — | 102.4 | — |
| | 0.1 mM | 96.8 | — | 96.6 | — |
| | 1 mM | 81.8 | — | 67.2 | Decrease |

"—" = neither increase nor decrease in peroxide level

Conclusion: In experiments where administration of the exemplary MNTF 4-mer (SEQ ID NO:11) was given at a concentration of 1 mM, endogenous peroxide level was reduced to 77.2% compared to that of the control and exogenous peroxide level was reduced to 54.9% of control. At a concentration of 10 mM, endogenous peroxide level was reduced to 0, and exogenous peroxide level was reduced to 25.2%. Thus, in this exemplary analysis, the test article comprising an exemplary 4-mer MNTF molecule, decreased both endogenous and exogenous peroxide levels from at 1 and 10 mM in a dose-dependent manner.

TABLE 4

Summary of Peroxide Levels (5-mer)

| Test Article | Conc. | % Control (no $H_2O_2$) | >25% Increase or Decrease in Peroxide Level | % Control (with $H_2O_2$) | >25% Increase or Decrease in Peroxide Level |
|---|---|---|---|---|---|
| CS2309, | 0.1 mM | 103.3 | — | 87.2 | — |
| Lot #D267 | 1 mM | 61.6 | Decrease | 46.2 | Decrease |
| Exemplary 5 mer | 10 mM | 3.6 | Decrease | −5.9 | Decrease |

TABLE 4-continued

Summary of Peroxide Levels (5-mer)

| Test Article | Conc. | % Control (no $H_2O_2$) | >25% Increase or Decrease in Peroxide Level | % Control (with $H_2O_2$) | >25% Increase or Decrease in Peroxide Level |
|---|---|---|---|---|---|
| Pal 5 mer | 0.01 mM | 95.3 | — | 98.6 | — |
| | 0.1 mM | 92.8 | — | 96.0 | — |
| | 1 mM | 83.6 | — | 62.2 | Decrease |

"—" = neither increase nor decrease in peroxide level

Conclusion: In experiments where administration of the exemplary MNTF 5-mer (SEQ ID NO:17) was given at a concentration of 1 mM, endogenous peroxide level was reduced to 61.6% compared to that of the control and exogenous peroxide level was reduced to 46.2% of control. At a concentration of 10 mM, endogenous peroxide level was reduced to 3.6%, and exogenous peroxide level was reduced to 0%. Thus, in this exemplary analysis, the test article CS2309, Lot #D267 comprising an exemplary 5-mer MNTF molecule, decreased both endogenous and exogenous peroxide levels from at 1 and 10 mM in a dose-dependent manner.

These data show affirmatively that exemplary MNTF molecules (e.g. 3-mer, 4-mer, 5-mer) are effective in reducing endogeneous and exogeneous peroxide levels in a dose dependent manner. The anti-oxidative activities of these representative molecules in the MNTF family of compounds confirm their utilities in reducing oxidative damage in the skin.

Example 7

Determination of the Protective Effects of Cosmetic Formulations Against UV Exposure In-vivo method for assessing the protective effects of cosmetic products. Bleaching of carotenoids have been used to evaluate the auto-oxidation activity of natural products. The relative efficacy of scavengers of lipid peroxyl free radicals after application to the skin was assessed by measuring the UVA-bleaching of beta-carotene as a function of the energy exposure.

Twelve healthy male and female subjects between the ages of nineteen (19) and sixty-four (64) years and of Fitzpatrick skin types I and II were selected in the study. Subjects who met the Inclusion Criteria signed an Informed Consent in conformity with 21 CFR Part 50: "Protection of Human Subjects" and completed a Panelist Profile/Medical History Form.

A CHROMAMETER colorimeter (TM, Minolta Model CR-300) was used to measure changes in color by expressing the color of measured surfaces numerically in L*a*b* color space which is a system recommended by the CIE (Commission Internationale de l'Eclairage) for skin color assessment. In this color space, L* is the luminance and gives the relative brightness from total black (L*=0) to total white (L*=100). The a* value represents the balance between the reds (positive values) and the greens (negative values). The b* value represents the balance between the yellows (positive values) and the blues (negative values). The b* value most closely describes the intensity of the orange color of the β-carotene stain and is in direct correlation with the Color Index, I. The CHROMAMETER provides a means by which oxidative damage caused by free radicals and, conversely, the prevention of oxidation by free radical scavengers, can be measured.

Free radical oxidation induced by UVA radiation elicits a bleaching and reduction of color of beta-carotene stain. The bleaching and prevention of bleaching by a test material can be measured by the CHROMAMETER. Bleaching is reported as the change in b* versus UVA Irradiation Energy. It can also be expressed in terms of a Color Index, I, defined as:

$$I=[(b_n*-b_i*)/(b_0*-b_i*)]\times 100$$

where, $b_n*$ is the value of b* measured after n $J/cm^2$ of irradiation of the area treated with the cosmetic formulation and painted with the β-carotene; $b_0*$ is the value of b* after application of the beta-carotene but before irradiation; and $b_i*$ is the value of b* before application of the beta-carotene. This index compensates for any effects of skin color on $b_n*$ and $b_0*$. Bleaching will cause $b_n*$ value and I value (as a percentage) to decrease. Prevention of bleaching will result in higher I values or less reduction in I value when exposed to radiation.

The designated forearm of impaneled subjects was cleansed with a 70% isopropyl alcohol prep pad (Medium, Dynarex) and allowed to dry. Test sites were selected on the volar surface of the designated forearm of each subject, with each test site defined by the open, central area of a self-adhesive ring (Professional ProFoot™ Products, P.P.R. Co, Inc.). The adhesive side of the rings were placed directly on the skin. The rings were used to retain the test material and beta-carotene solution as well as to function as a guide for taking measurements with the CHROMAMETER.

Gel formulations (0.1% Pal-hexapeptide) and (0.1% hexapeptide) were applied to the forearm according to a randomized schedule. Additional sites were treated with a beta-carotene control, a positive control (internal control) and an untreated control. Treatment of the test sites were randomized for each subject.

Prior to application of the test materials or beta-carotene, the initial b* parameter was measured using the CHROMAMETER and recorded for all duplicate test sites of the forearm (Baseline). Approximately 2 $mg/cm^2$ of each material was applied to the designated test site and spread manually with a finger cot to ensure even distribution. Sites designated as untreated, with or without beta-carotene, remained untreated at this time. The test materials and internal control were allowed to incubate with the skin surface for a period of fifteen (15) minutes. After this incubation period, b* measurements were recorded for all sites (Product Baseline).

A solution of beta-carotene in a mixture of capric and caprylic triglycerides was applied to all treated sites. The b* parameter is again measured and recorded (beta-carotene Baseline).

Long wavelength UVA (320-420 nm) was used because it is less likely to elicit burning of the skin than UVB irradiation (290-320 nm) and is known to contribute to the formation of free radicals.

Figure 4A:
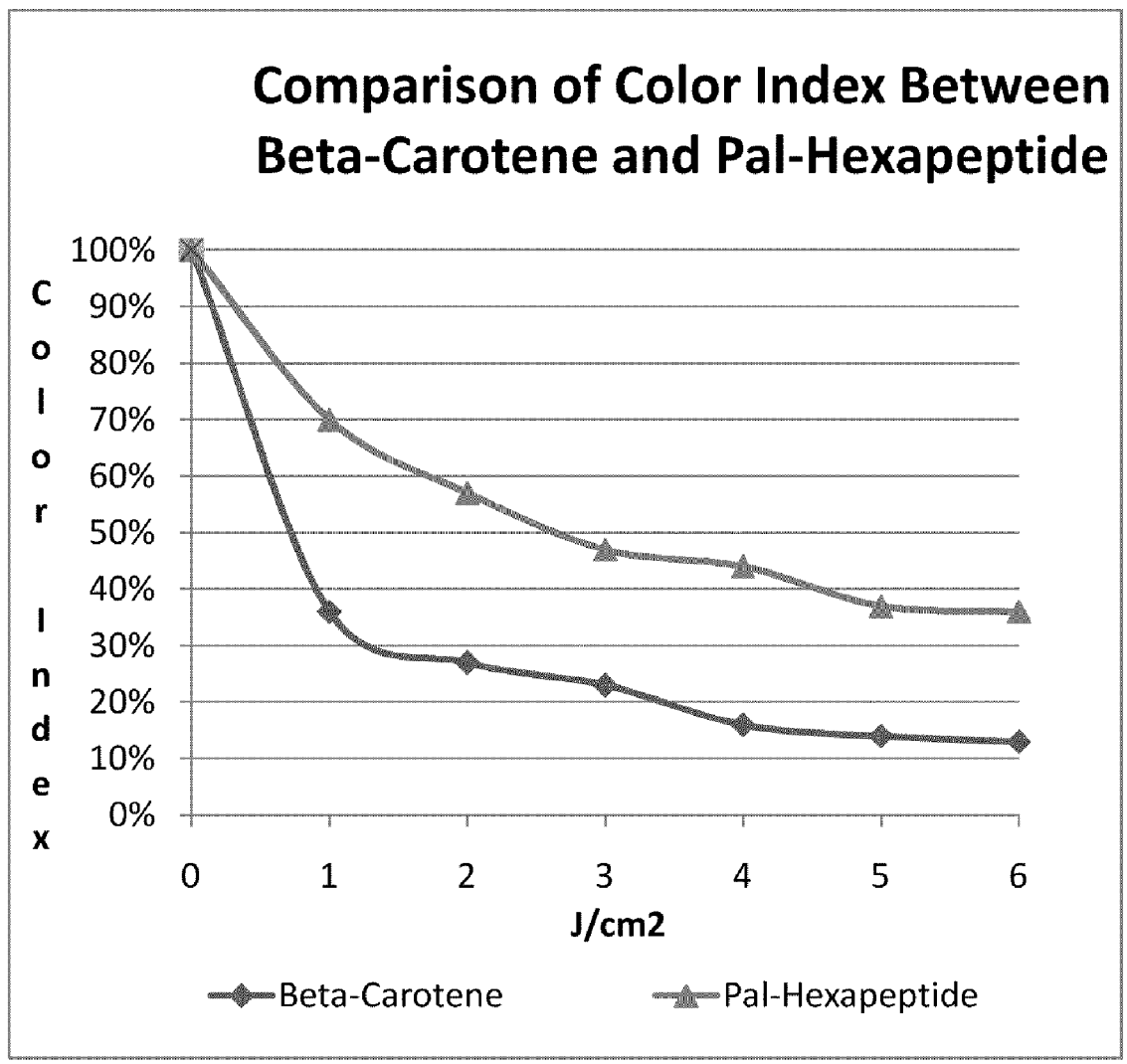
FIG. 4A is a graph that compares color indices corresponding to beta-carotene (diamonds) and to an MNTF peptide (Pal-Hexapeptide; triangles) described herein, as measured by the reduction of UV (UVA)-induced free radical bleaching of β-carotene (i.e., an indicator of anti-oxidative capacity).
Figure 4B:
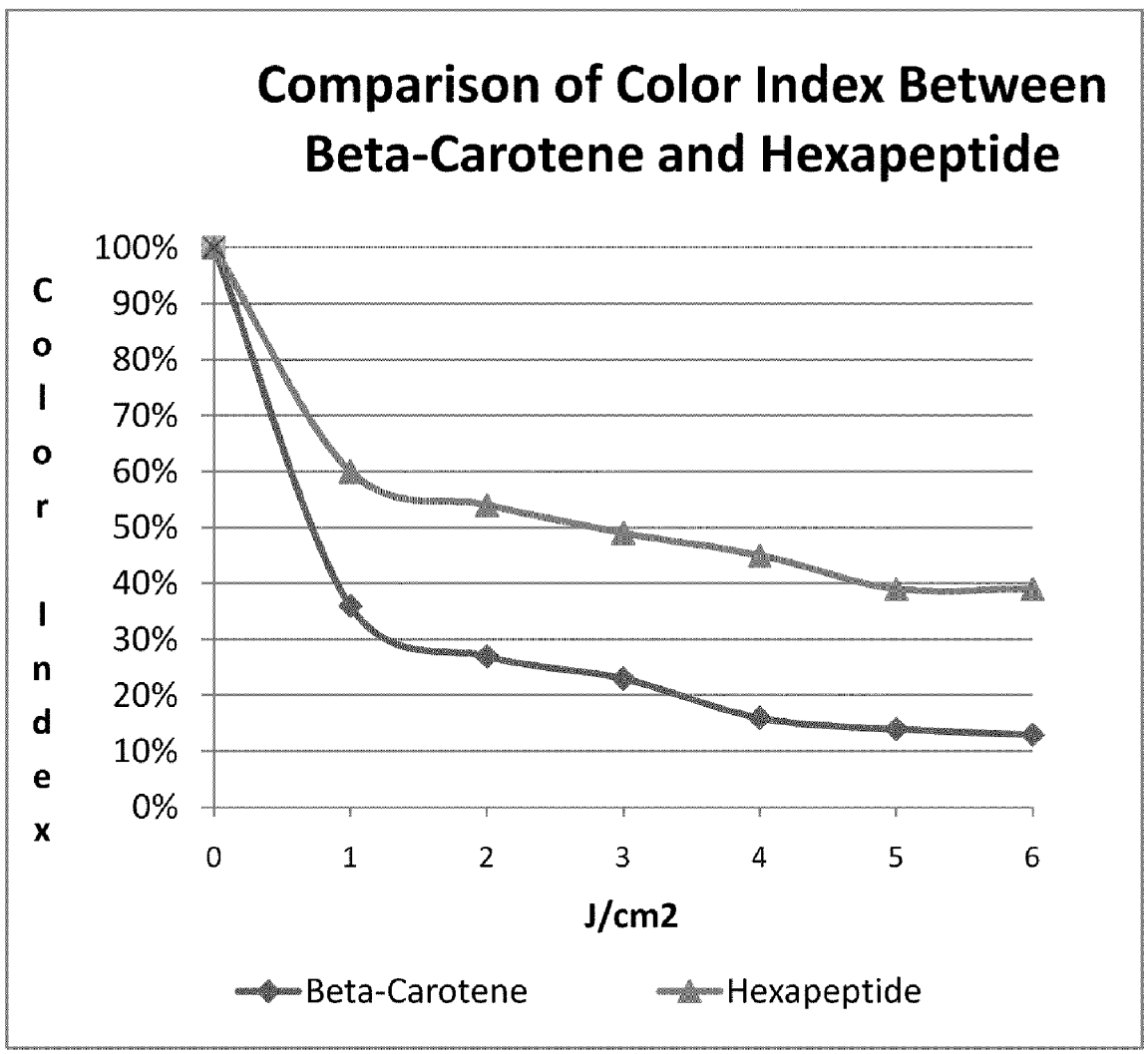
FIG. 4B is a graph that compares color indices corresponding to beta-carotene (diamonds) and an MNTF hexapeptide ("Peptide"; triangles) described herein, as measured by measuring the reduction of bleaching of β-carotene.

The subject's forearm was exposed to approximately 1.0 J/cm² of UVA radiation using a sun lamp, and the b* parameter is again measured by the CHROMAMETER and recorded. This phase of the test method was repeated for five (5) additional energy exposures at 2.0, 3.0, 4.0, 5.0 and 6.0 J/cm² of UVA radiation. The results are shown in FIGS. 4A and 4B.

The color index was calculated for each of the duplicate test material sites.

Preparation of Beta-Carotene Solution

Thirty (30) milliliters of a saturated solution of beta-carotene in a mixture of capric and caprylic triglycerides (44:55), manufactured by Stepan Company, was measured in a test tube. Approximately 0.70 grams of beta-carotene wais added to the triglyceride solution and heated over a hotplate to 100° C. for approximately two (2) minutes until the mixture becomes a dark orange/red color. The solution was filtered to remove any excess beta-carotene and is refrigerated to prevent oxidation. The solution was discarded when evidence of oxidation, changes in color from dark orange/red to light yellow/orange was observed.

Color Index values for site treated with each test or control material were compared statistically using analysis of variance (ANOVA). Statistical significance exists for all p-values less than or equal to 0.05 at the 95% confidence level. A Dunnett's Test was used to determine the significance of differences between each treatment product and the control at the 95% confidence level.

Protective effects of Pal-hexapeptide and hexapeptide were measured and compared with beta-carotene alone by assessing the UVA bleaching of beta-carotene as a function of irradiated energy.

The average Color Index Value measured by CHROMAMETER for Pal-hexapeptide, hexapeptide and for beta-carotene tested at 0, 1.0, 2.0, 3.0, 4.0, 5.0, 6.0 J/cm² are summarized in the following table.

|  | Energy J/cm² | | | | | | |
| --- | --- | --- | --- | --- | --- | --- | --- |
|  | 0 | 1 | 2 | 3 | 4 | 5 | 6 |
| (0.1% Pal-hexapeptide) gel | 100% | 70% | 57% | 47% | 44% | 37% | 35% |
| PC (beta-carotene) | 100% | 36% | 27% | 23% | 16% | 14% | 13% |
| P value |  | 0.0001 | 0.0002 | 0.0024 | 0.0002 | 0.0033 | 0.0016 |
| Oligopeptide (0.1% hexapeptide) gel | 100% | 60% | 54% | 49% | 45% | 39% | 39% |
| PC (beta-carotene) | 100% | 36% | 27% | 23% | 16% | 14% | 13% |
| P value |  | 0.0001 | 0.0006 | 0.0044 | 0.0003 | 0.0016 | 0.0028 |

The free radical oxidation induced by UVA radiation elicits a bleaching of beta-carotene, and the Color Index I shows bigger decrease in I value as radiation energy increased. Comparing sites treated with Pal-hexapeptide or hexapeptide and beta-carotene with sites treated with beta-carotene alone, the Pal-hexapeptide or hexapeptide treated sites have higher I values, i.e. Pal-hexapeptide or hexapeptide is capable of preventing the bleaching of beta-carotene compared to the beta-carotene control. On this basis, Pal-hexapeptide and hexapeptide were demonstrated to be effective as a free radical scavenger. Skin data for 6 mer non-pal: included together with pal 6 mer Example 8

Effect of MNTF On Inhibition of Human Keloid Scar Formation

Keloid can be characterized as a hyperproliferation/growth of fibrous scar tissue following trauma to the skin. Example 8 demonstrates the efficacy of exemplary MNTF/MNTF analog molecules in dermal applications as measured by a human keloid fibroblast proliferation kinetic study. Experimental protocols were based on a published study design for keloid fibroblast growth kinetics and is as described in Polo et al., 1999, Ann. Plastic Surg. 43 (2):185-190.

Briefly, fibroblasts were cultured from skin tissue obtained from fresh surgical specimens. The skin specimen was rinsed in 10 ml of calcium- and magnesium-free Dulbecco's phosphate-buffered saline (Sigma Chemical Co, St. Louis, Mo.) supplemented with gentamycin (20 mg per milliliter) for 30 minutes at room temperature. A second antibiotic rinse using 1% 10,000 U per milliliter penicillin G, 25 micrograms per milliliter amphotericin B, 10,000 micrograms per milliliter streptomycin sulfate solution (Gibco BRL, Gran Island, N.Y.) was performed for 10 minutes. The epidermis was separated from the dermis from each piece. The specimen was cut into four pieces of equal dimensions. Each piece was placed dermis-side down into a 60-mm culture dish containing Dispase solution (Collaborative Biomedical Products, Bedford, Mass.). The explants were incubated with no additional culture media for 15 minutes at 37° C. A total of 10 ml Dulbecco's modified Eagle's medium (DMEM; Gibco BRL) was added slowly to the culture dish, which was then incubated at 37° C. at 5% carbon dioxide. The cells were subcultured until 80% confluence was obtained. Trypsin-ethylenediaminetetraacetic acid (Gibco BRL) was added to lyse the cells from the surface of the culture plate, and the cells were washed with DMEM and transferred to a centrifuge tube. The cultures were centrifuged at 1,000 g for 5 minutes. The supernatant was decanted and the cell pellets were resuspended in 5 ml DMED. This rinse/wash and 5-minute centrifuge was repeated three times. The cells were counted using a hemocytometer, and their cell number was adjusted to 1×10⁶ cells, which were then plated on a 35-mm Petri dish with 2 ml DMED and 1% fetal bovine serum, and incubated at 37° C. in 5% carbon dioxide. 10 ml of exemplary MNTF/analog solution is added in the Petri dish with 100,000 cells.

Samples from each group were removed on days 1, 2, 3 and 4. The cells from each sample were trypsinized, washed, centrifuged, and resuspended in 1 ml DMEM; and were counted using the Trypan blue dye exclusion method and a hemocytometer. Results are shown in FIG. 1.

Results indicated that inhibition of human keloid fibroblast cells by MNTF is statistically significant. P<0.003 on Day 2. Dose response study using these parameters indicated that MNTF concentration at $10^{-5}$ M or 10 micrograms per milliliter is highly effective.

Example 8

Stimulation of Hylauronic Acid By MNTF

Hyaluronic acid (hyaluronan, HA), a naturally occurring carbohydrate polymer is a key component of connective, epithelial and neural tissues. HA participates in hydrodynamics, movement and proliferation of cells. This test was designed to determine whether a sample of palmitylated and non-palmitylated MNTF hexapeptide has an effect on hyaluronic acid levels in the adult human dermal fibroblast (aHDF) conditioned media.

Methods

Pal-Hexapeptide

Adult HDF (facial, passage 2, Cell Applications, San Diego, Calif. cat.#106-05A lot#1392) were plated in high glucose phosphate-free DMEM supplemented with 5% cosmic serum from Hyclone, Utah) at 6,000 cells per well and test materials were added the following day. Test materials were: Pal-Hexapeptide (palmitylated SEQ ID NO:2 as a lyophilized powder labeled APC 341055, lot V08150A1, received from DermaCare Neuroscience Institute), type I sterile water (negative control) and basic fibroblast growth factor (bFGF, positive control). Pal-Hexapeptide was dissolved in water at 20 mg/ml. Final concentrations tested were: 400, 200, 100, 50 and 25 ug/ml for DNP and 5 ng/ml for bFGF (plate 507). After 96 h, cell culture conditioned media were collected and 100 ul aliquotes were used for the HA assay. HA assay was performed using Hyaluronan Enzyme-Linked Immunosorbent Assay Kit (HA-ELISA, cat. #K-1200) from Echelon (Salt Lake City, Utah). The HA output was measured by following the generation of a chromophoric reaction product in 96 well plate, with the use of a BioRad microplate reader at 410 nm and the effect of the test materials was determined using the formula: Absorbance 410 (sample)/Absorbance 410 (Zero HA)×100.

Figure 5A:
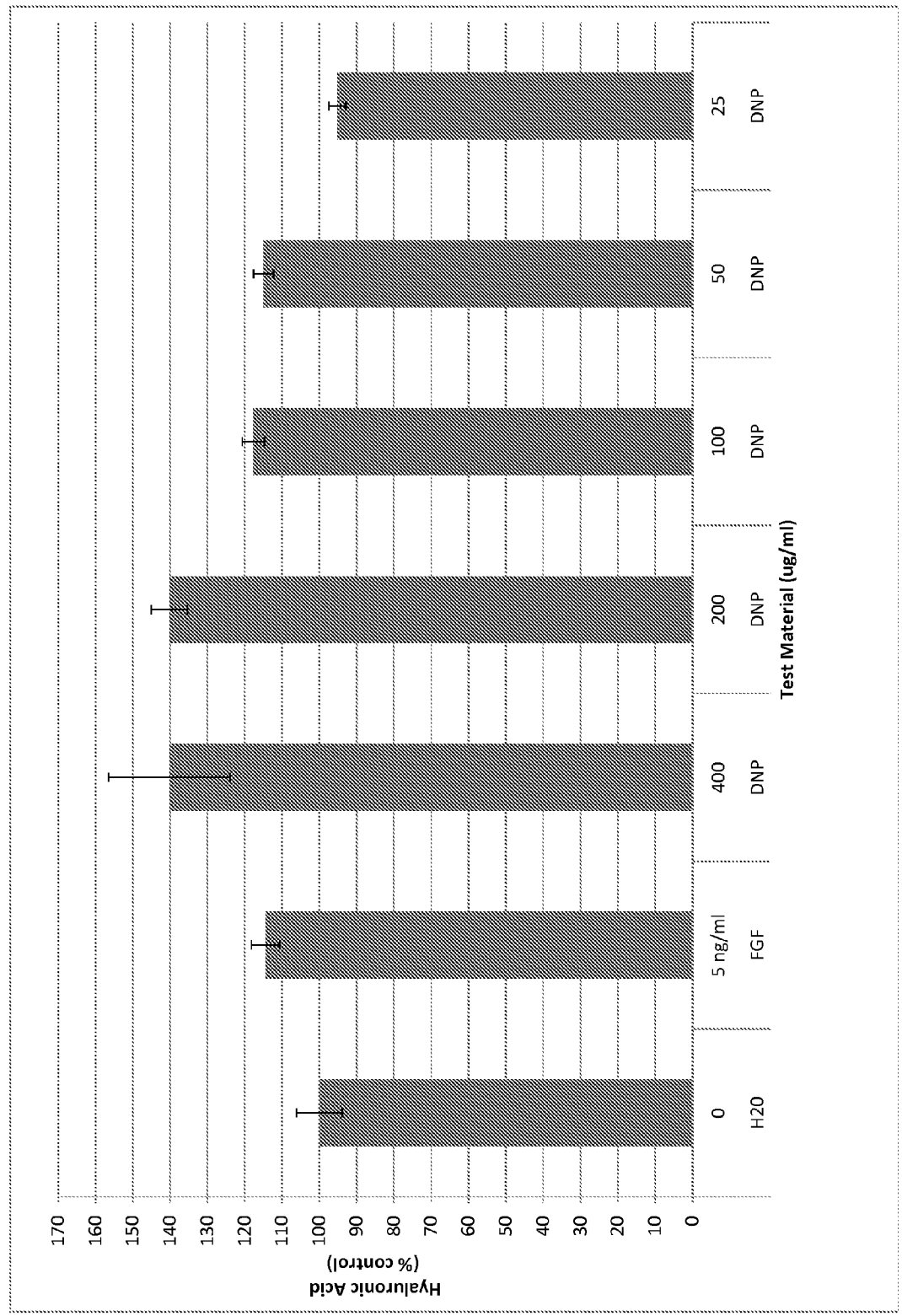
FIG. 5 is a bar graph that shows the effect of palmitylated MNTF hexapeptide (FIG. 5A) and non-palmitylated MNTF hexapeptide (FIG. 5B) in stimulating hyaluronic acid in the fibroblast.

As illustrated on the FIG. 5A, Pal-Hexapeptide strongly stimulated hyaluronic acid in the fibroblast-conditioned medium at 400 ug/ml and 200 ug/ml (40% stimulation), and moderately (by about 15%) at 100 and 50 ug/ml. The positive control (bFGF) had a moderately stimulatory activity at the concentration tested demonstrating the technical success of the experiment.

Non-Palmitylated Hexapeptide

Adult HDF (facial, passage 2, Cell Applications, San Diego, Calif. cat.#106-05A lot#1392) were plated in high glucose phosphate-free DMEM supplemented with 5% cosmic serum from Hyclone, Utah) at 6,000 cells per well and test materials were added the following day. Test materials were: hexapeptide (SEQ ID NO:2 (non-palmitylated), lyophilized powder lot #D294, received from DermaCare Neuroscience Institute), type I sterile water (negative control) and basic fibroblast growth factor (bFGF, positive control). Pal-Hexapeptide was dissolved in water at 20 mg/ml. Final concentrations tested were: 2000, 1000, 500 and 250 ug/ml for hexapeptide and 5 ng/ml for bFGF (plate 507). After 96 h, cell culture conditioned media were collected and 100 ul aliquotes were used for the HA assay. HA assay was performed using Hyaluronan Enzyme-Linked Immunosorbent Assay Kit (HA-ELISA, cat. #K-1200) from Echelon (Salt Lake City, Utah). The HA output was measured by following the generation of a chromophoric reaction product in 96 well plate, with the use of a BioRad microplate reader at 410 nm and the effect of the test materials was determined using the formula: Absorbance 410 (sample)/Absorbance 410 (Zero HA)×100.

Figure 5B:
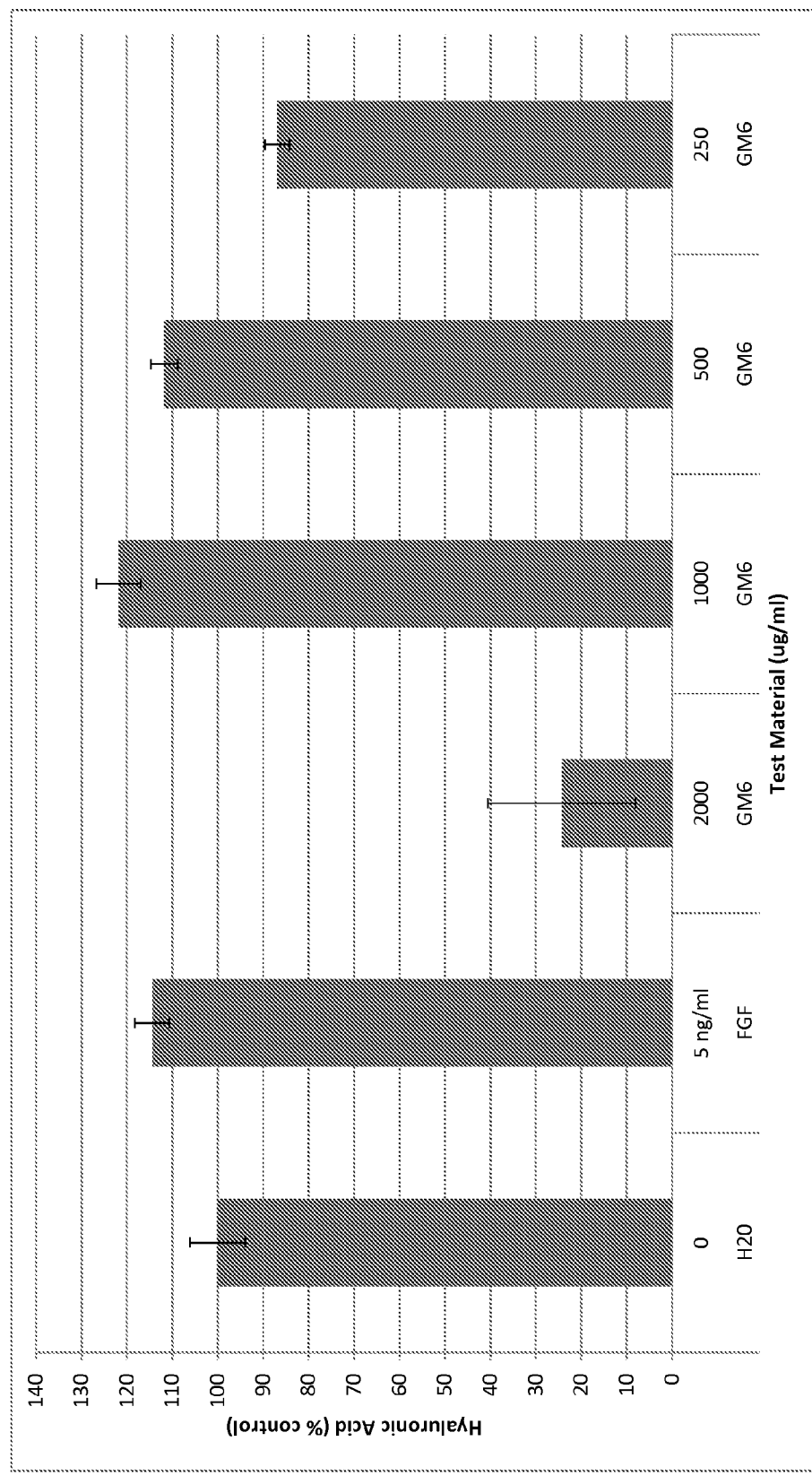

As illustrated on the FIG. 5B, the non-palmitylated hexapeptide had a good stimulatory activity on hyaluronic acid in the fibroblast-conditioned medium at 1000 ug/ml (22% stimulation). The positive control (bFGF) had a moderately stimulatory activity at the concentration tested demonstrating the technical success of the experiment.

All patents, publications, scientific articles, web sites, and other documents and materials referenced or mentioned herein are indicative of the levels of skill of those skilled in the art to which this disclosure pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of some embodiments and are exemplary and not intended as limitations on the scope of the appended claims. Other objects, aspects, and embodiments will occur to those skilled in the art upon consideration of this specification, and are encompassed within the spirit of the disclosure as defined by the scope of the claims. It will be readily apparent to one skilled in the art that varying substitutions and modifications can be made to the technology disclosed herein without departing from its scope and spirit. The technology illustratively described herein suitably can be practiced in the absence of any element or elements, or limitation or limitations, which is not specifically disclosed herein as essential.

What is claimed is:

1. A topical skin rejuvenating or protecting composition comprising:
   a) an effective amount of a MNTF peptide having the amino acid sequence comprising of SEQ ID NO:11; and
   b) a cosmetically, dermatologically or pharmaceutically acceptable carrier.

2. The composition according to claim 1, wherein said MNTF peptide is modified by covalent linkage with a penetration enhancer, whereby the tissue penetration ability of the composition is improved.

3. The composition according to claim 2, wherein said MNTF peptide is N-terminally modified by covalent linkage to said penetration enhancer.

4. The composition according to claim 3, wherein said penetration enhancer is covalently attached to said MNTF peptide by N-acyl derivatives of free amino groups.

5. The composition according to claim 4, wherein said penetration enhancer is an optionally substituted alkyl carboxylic acid of 2 to 22 carbons, wherein said alkyl carboxylic acid is optionally hydroxylated, unsaturated, and/or sulfurated.

6. The composition according to claim 5, wherein said penetration enhancer is a fatty acid is selected from cabrylic acid, oleic acid, lauric acid, capric acid, caprylic acid, hexanoic acid, myristic acid, palmitic acid, valeric acid, stearic acid, linoleic acid, linolenic acid, arachidonic acid, oleic acid, elaidic acid, erucic acid, nervonic acid.

7. The composition according to claim 1, wherein:
   (a) the amount of peptide is encapsulated in a vector selected from the group consisting of macro-capsules, micro-capsules, nano-capsules, liposomes, chylomicrons and microsponges, or
   (b) said peptide is absorbed on a material selected from the group consisting of powdered organic polymers, tales, bentonites, and other mineral supports, or
   (c) said peptide is mixed with other ingredients selected from a group comprising extracted lipids, vegetable extracts, liposoluble active principles, hydrosoluble active principles, anhydrous gels, emulsifying polymers, tensioactive polymers, synthetic lipids, gelifying polymers, tissue extracts, marine extracts, Vitamin A, Vitamin C, Vitamin D, Vitamin E, solar filters, and antioxidants.

8. A method for rejuvenating or protecting skin, the method comprising topically administering a composition according to claim 1 to a subject, wherein the composition is administered in an amount effective to promote the rejuvenation or protection of skin.

9. The method according to claim 8, wherein the method reduces or inhibits photodamage associated inflammation or free radical damage in a subject in need thereof.

10. The method according to claim 8, wherein the method reduces peroxides or free radical generation in the skin in a subject in need thereof.

11. The method according to claim 8, wherein the method reduces wrinkles in a subject in need thereof.

12. The method according to claim 8, wherein the method improves skin tone in a subject in need thereof.

13. The method according to claim 8, wherein the method reduces UV or photodamage in the skin in a subject in need thereof.

14. The method according to claim 8, wherein the method promotes skin regeneration in a subject in need thereof.

\* \* \* \* \*